US012735733B2

(12) United States Patent
Neely et al.

(10) Patent No.: US 12,735,733 B2
(45) Date of Patent: Sep. 15, 2026

(54) LABELLING OF BIOMOLECULES

(71) Applicant: TAGOMICS LIMITED, Coventry (GB)

(72) Inventors: Robert Neely, Birmingham (GB); Francisco Fernandez-Trillo, Birmingham (GB); Elodie Jagu, Birmingham (GB); Andrew Wilkinson, Birmingham (GB)

(73) Assignee: TAGOMICS LIMITED, Coventry (GB)

(*) Notice: Subject to any disclaimer, the term of this patent is extended or adjusted under 35 U.S.C. 154(b) by 1214 days.

(21) Appl. No.: 17/761,817

(22) PCT Filed: Sep. 18, 2020

(86) PCT No.: PCT/GB2020/052264

§ 371 (c)(1),
(2) Date: Mar. 18, 2022

(87) PCT Pub. No.: WO2021/053347

PCT Pub. Date: Mar. 25, 2021

(65) Prior Publication Data

US 2022/0340946 A1 Oct. 27, 2022

(30) Foreign Application Priority Data

Sep. 20, 2019 (GB) ..................................... 1913598

(51) Int. Cl.
*C12P 19/34* (2006.01)

(52) U.S. Cl.
CPC .................................... *C12P 19/34* (2013.01)

(58) Field of Classification Search
CPC ............................... C07H 19/167; C12P 19/34
See application file for complete search history.

(56) References Cited

U.S. PATENT DOCUMENTS 7,364,911 B2 4/2008 Aebersold et al.
8,168,405 B2 5/2012 Darzins et al.
(Continued)

FOREIGN PATENT DOCUMENTS

CN 1602422 A 3/2005
CN 101115995 A 1/2008
(Continued)

OTHER PUBLICATIONS

Bandyopadhyay et al., "Fast and selective labeling of N-terminal cysteines at neutral pH via thiazolidino boronate formation", Chem. Sci., vol. 7, pp. 4590-4593 (2016).
(Continued)

*Primary Examiner* — Jezia Riley
(74) *Attorney, Agent, or Firm* — Caesar Rivise, PC

(57) ABSTRACT

A method of reversibly labeling a biomolecule including providing a linker molecule (11) having a first functional group (LG) with a reactive center, a second functional group (FG) with a reactive center, and a cleavable, e.g. hydrolyzable, moiety (A-B—C). The method further includes forming a covalent bond between the biomolecule (10) and the reactive center of the first functional group (LG), forming a covalent bond between a first label (L1) and the reactive center of the second functional group (FG), cleaving the cleavable moiety (A-B—C), e.g. hydrolyzing the hydrolyzable moiety, of the linker molecule (11) to remove the first label (L1) and to form a third functional group (W) with a reactive center, and forming a covalent bond between a further molecule and the reactive center of the third functional group (W) to reform the cleavable moiety, e.g. hydrolyzable moiety (A-B—C).

18 Claims, 10 Drawing Sheets

(56) References Cited

U.S. PATENT DOCUMENTS

| | | | |
|---|---|---|---|
| 2007/0161007 | A1 | 7/2007 | Rajski et al. |
| 2009/0018101 | A1 | 1/2009 | Weinhold et al. |
| 2010/0297250 | A1 | 11/2010 | Boons et al. |
| 2012/0178086 | A1 | 7/2012 | Franzini et al. |
| 2017/0283453 | A1 | 10/2017 | Neely et al. |

FOREIGN PATENT DOCUMENTS

| | | | |
|---|---|---|---|
| EP | 1712557 | A1 | 10/2006 |
| EP | 2594651 | A1 | 5/2013 |
| WO | 2006108678 | A2 | 10/2006 |
| WO | 2012105596 | A1 | 8/2012 |
| WO | 2018187382 | A1 | 10/2018 |

OTHER PUBLICATIONS

Benizri et al., "Bioconjugated Oligonucleotides: Recent Developments and Therapeutic Applications", Bioconjugate Chem., vol. 30, pp. 366-383 (2019).

Deen et al., "Methyltransferase-Directed Labeling of Biomolecules and its Applications", Angew. Chem. Int. Ed., vol. 56, pp. 5182-5200 (2017).

Li et al., "Chemoenzymatic Methods for the Synthesis of Glycoproteins", Chem. Rev., vol. 118, pp. 8359-8413 (2018).

Loakes et al., "Polymerase engineering: towards the encoded synthesis of unnatural biopolymers", Chem. Commun., pp. 4619-4631 (2009).

Sarac et al., "Terminal Deoxynucleotidyl Transferase in the Synthesis and Modification of Nucleic Acids", ChemBioChem, vol. 20, pp. 860-871 (2019).

Stenton et al., "A thiotetheher-directed palladium-cleavable linker for targeted bioorthogonal drug decaging", Chem Sci., vol. 9, pp. 4185-4189 (2018).

Yu et al., "Highly Reactive and Tracelessly Cleavable Cysteine-Specific Modification of Proteins via 4-Substituted Cyclopentenone", Angew. Chem. Int. Ed., vol. 57, pp. 11598-11602 (2018).

Zhang et al., "Recent progress in enzymatic protein labelling techniques and their applications", Chem. Soc. Rev., vol. 47, pp. 9106-9136 (2018).

Anhauser et al. (2018). Reversible modification of DNA by methyltransferase-catalyzed transfer and light-triggered removal of photo-caging groups. Chemical Communications, 54(5), 449-451.

Bothwell et al. (2012). Se-adenosyl-L-selenomethionine cofactor analogue as a reporter of protein methylation. Journal of the American Chemical Society, 134(36), 14905-14912.

Bothwell et al. (2014). Large-scale, protection-free synthesis of Se-adenosyl-L-selenomethionine analogues and their application as cofactor surrogates of methyltransferases. Organic letters, 16(11), 3056-3059.

Flade et al. (2017). The N6-position of adenine is a blind spot for TAL-effectors that enables effective binding of methylated and fluorophore-labeled DNA. ACS chemical biology, 12(7), 1719-1725.

Holstein et al. (2014). Bioorthogonal site-specific labeling of the 5'-cap structure in eukaryotic mRNAs. Chemical Communications, 50(34), 4478-4481.

Hoyt et al. (2019). Contemporary approaches to site-selective protein modification. Nature Reviews Chemistry, 3(3), 147-171.

Islam et al. (2011). Expanding cofactor repertoire of protein lysine methyltransferase for substrate labeling. ACS chemical biology, 6(7), 679-684.

Plotnikova et al. (2014). Selective covalent labeling of miRNA and siRNA duplexes using HEN1 methyltransferase. Journal of the American Chemical Society, 136(39), 13550-13553.

Vranken et al. (2014). Super-resolution optical DNA Mapping via DNA methyltransferase-directed click chemistry. Nucleic acids research, 42(7), e50, 1-21.

Search Report from corresponding GB 1913598.7 mailed Mar. 24, 2020.

International Search Report from corresponding PCT/GB2020/052264 mailed Dec. 15, 2020.

Dirksen et al. (2010). Bisaryl hydrazones as exchangeable biocompatible linkers. Angew. Chem. Int. Ed., 49, 2023-2027.

Wilkinson et al. (2020). Site-selective and rewritable labeling of DNA through enzymatic, reversible, and click chemistries. ACS Central Science, 6, 525-534.

Chen et al. (2015). Label-free electrochemical study on DNA methyltransferase activity. Chemical Sensors, 35(3).

Zhao. (2015). Related research progress in DNA methylation. Medical Recapitulate, 21(8), 1359-1361.

English Abstract for WO 2012105596 A1 (2012).

21A

21B

22

3

7 8 1

4

9 10 11 4

LABELLING OF BIOMOLECULES

CROSS-REFERENCE TO RELATED APPLICATIONS

This application is a U.S. National Phase Application of PCT/GB2020/052264, filed Sep. 18, 2020, which claims priority to GB 1913598.7, filed Sep. 20, 2019, the contents of which applications are incorporated herein by reference in their entireties for all purposes.

FIELD OF THE INVENTION

This invention relates generally to the labelling of biomolecules. More specifically, although not exclusively, this invention relates to a method of reversibly labelling biomolecules.

BACKGROUND OF THE INVENTION

Bioconjugation is a chemical strategy in which a covalent bond is formed between a biomolecule and second molecule. The second molecule may act as a tag or label, in which case the second molecule will impart new properties to the biomolecule. The second molecule may impart properties that are suitable for use in measuring the location and/or concentration of the biomolecule, for example, to track cellular events, determine enzyme function, measure drug delivery, and so on. The second molecule may be, for example, a fluorescent molecule, a radioactive species, and/or a different biomolecule suitable for use in a detection assay. Alternatively, the second molecule may be selected such that it renders the biomolecule more soluble or more stable in a certain environment. In other cases, the second molecule may be used for targeting another biomolecule.

A few simple conjugation chemistries dominate those applied for the site-selective, chemical modification (or functionalization) of biomolecules (for example, Hermanson, G. T. Bioconjugate Techniques, 2013; Bioconjugated Oligonucleotides: Recent Developments and Therapeutic Applications. Bioconjug. Chem. 2019; Contemporary Approaches to Site-Selective Protein Modification. Nat. Rev. Chem. 2019). These chemistries underpin a diverse range of manipulations, sorting and labelling experiments upon which subsequent analyses typically depend.

Invariably, however, the focus of these methodologies has been on developing stable linkages between the target biomolecule and the requisite functional moiety. Hence, functionalization can limit the study of a biomolecule to a single analytical process. This approach is at odds with recent studies in cell biology, where integrative approaches to observing cell behaviours are becoming increasingly important.

Recent efforts to address one or more of these problems include the following prior art. Bernardes et al. have reported the development of a bifunctional linker that simultaneously allows site-specific protein modification and palladium-mediated bio-orthogonal decaging. This was enabled by a thioether binding motif in the propargyl carbamate linker and a readily available palladium complex (Bernardes et al. Chem. Sci., 2018, 9, 4185, Angew. Chem. Int. Ed. Vol 57, 36, 2018; Chem. Sci., 2016,7, 4589-4593).

It has also been reported to use cleavable diazo bonds in the capture and release of proteins as a tool to monitor the activity of endogenous methyltransferase enzymes (Luo et. al., J. Am. Chem. Soc. 2012, 134, 36, 14905-14912). After labelling and capture, proteins can be released by cleavage of the diazo group with sodium dithionite.

A reversible mTAG labelling strategy has been reported in which the label moiety is removed using UV light (see Chem. Commun., 2018,54, 449-451). The light-triggered removal was absolute, meaning that repeat labelling of the DNA molecule was necessary. In addition, the label moiety did not comprise functionality for further functionalisation.

It is therefore a first non-exclusive object of the invention to provide a bio-orthogonal method of reversibly linking a biomolecule to a second molecule, for example, a label. It is a further non-exclusive object of the invention to provide a bio-orthogonal method of labelling, un-labelling, and re-labelling a biomolecule in an endless cycle such that multiple analyses may be sequentially performed on a single sample. It is a further non-exclusive object of the invention to provide a bio-orthogonal method of recovering the second or further molecule(s). SUMMARY OF THE INVENTION Accordingly, a first aspect of the invention provides a method of reversibly labelling a biomolecule, the method comprising:

a. providing a linker molecule, the linker molecule comprising a first functional group comprising a reactive centre, a second functional group comprising a reactive centre, and a cleavable, e.g. hydrolysable, moiety;
b. forming a covalent bond between the biomolecule and the reactive centre of the first functional group;
c. forming a covalent bond between a first label and the reactive centre of the second functional group;
d. cleaving the cleavable moiety, e.g. hydrolysing the hydrolysable moiety, of the linker molecule to remove the first label and to form a third functional group comprising a reactive centre;
e. forming a covalent bond between a further molecule and the reactive centre of the third functional group to reform the cleavable moiety, e.g. hydrolysable moiety.

Advantageously, the cleavable moiety or bond, e.g. hydrolysable moiety or bond, of the linker molecule in the method of the invention may be used to site-selectively write, modify, erase, and rewrite functionality onto the biomolecule in an integrative approach. The method of the invention may be used for example, in single-cell analyses, where material is limited. By using the method of the invention to combine multiple analytical methods, new, more holistic understanding of cell behaviour is possible. More advantageously, the linker molecule, the label, and the biomolecule may be recovered after the required analysis has been performed.

In embodiments the cleavable moiety is a hydrolysable moiety. The hydrolysable moiety may be a Schiff base, for example, an imine moiety, an oxime moiety and/or a hydrazone moiety.

In embodiments, the hydrolysable bond may comprise a disulphide (S—S) bond.

In embodiments, the further molecule may comprise a fourth functional group comprising a reactive centre. The fourth functional group may be the same functional group as that of the second functional group.

In embodiments, the method may further comprise step f. forming a covalent bond between a second label and the reactive centre of a fourth functional group. In embodiments, the method may further comprise step g. cleaving the cleavable moiety, e.g. hydrolysing the hydrolysable moiety e.g. the Schiff base moiety, to remove the second label and to reform the third functional group. In embodiments, the method may further comprise step h. forming a covalent bond between a further molecule and the third functional group to reform the cleavable moiety, e.g. the hydrolysable moiety, e.g. the Schiff base moiety. In embodiments, the further molecule of step e. may be the same species as step h.

In embodiments, step c. is performed before step b. In alternative embodiments, step b. is performed before step c.

In embodiments, step b. may comprise a prior or contemporaneous step of removing a leaving group to expose the reactive centre of the first functional group. In embodiments, step c. may comprise a prior or contemporaneous step of removing a leaving group to expose the reactive centre of the second functional group.

In embodiments, the further molecule may comprise a label. The method may comprise step i., forming a covalent bond between a further molecule comprising a label and the third functional group to reform the cleavable moiety, e.g. the hydrolysable moiety, e.g. the Schiff base moiety. It is to be understood that this species may take the place of the reaction product of step c in the method of the invention. For example, the cleavable moiety, e.g. the hydrolysable moiety, may be hydrolysed to remove the label and to form a functional group (e.g. the third functional group) comprising a reactive centre. The method may further comprise forming a covalent bond between a further molecule and the reactive centre of the functional group (e.g. the third functional group) to reform the cleavable moiety, e.g. hydrolysable moiety.

In embodiments, step c, d, e, f, and g may be performed sequentially and repeated in an endless or closed cycle. Advantageously, this enables reversible labelling of the biomolecule with a first label, a second label, and an $n^{th}$ label sequentially.

The linker molecule may have the following general formula:

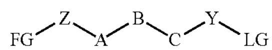

wherein FG represents the second functional group comprising a reactive centre;

Z represents a non-reactive group selected from one of an aliphatic linkage or an aromatic linkage;

A-B—C together represent the cleavable moiety, e.g. the hydrolysable moiety (e.g. the Schiff base moiety);

Y represents a non-reactive group selected from an aliphatic linkage or an aromatic linkage;

LG represents a first functional group comprising a reactive centre.

In embodiments, the reactive centre of the first, second, or third, or $n^{th}$ functional group may comprise a carbocation. In alternative embodiments, the first, second, third, or $n^{th}$ functional group may represent the reactive centre, for example, the reactive centre may comprise an azide moiety, e.g. in a click chemistry reaction with an alkyne moiety, e.g. on the first label. The reactive centre may comprise an alkene, or an alkyne moiety, e.g. which undergoes reaction with an azide moiety, e.g. on the first label.

In embodiments, the second functional group FG may be selected from one of a halide (e.g. an F, Cl, Br, or I atom), an unsaturated bond (e.g. an alkene, an alkyne), an azide, an activated ester, an activated carbonate, a carbamate, an epoxide, an isothiocyanate, or an isocyanate moiety.

Preferably, the second functional group FG is an azide moiety.

In embodiments, the first functional group LG is a functional group or chemical entity that allows the site-selective labelling of a biomolecule via chemical or enzymatic methods.

In embodiments, the first functional group LG may be selected from one of a halide, a sulphonate (e.g. mesylate, tosylate), an iodonium salt, an acetate, an acrylate (e.g. methacrylate), an acrylamide (e.g. methacrylamide), maleimide (e.g. bromomaleimide, dibromomaleimide), bromopyridazinedione, propargylester, propagylamide, α-bromoester, α-bromoamide, 3-arylproiolonitrile, —$CH_2$-substituted trivalent sulphonium ion, a halide (e.g. an F, Cl, Br, or I atom), an unsaturated bond (e.g. an alkene, an alkyne), an azide, an activated ester, and activated carbonate, a carbamate, an epoxide, an isothiocyanate, or an isocyanate moiety.

In embodiments, the first functional group LG may comprise a diazonium salt or a diazocarboxylate, for example, to undergo reaction with a phenol (e.g. tyrosine) on a biomolecule.

In a preferred embodiment, the first functional group LG comprises a nitrile moiety, e.g. 3-arylpropiolonitrile, for example, to undergo a site-selective reaction with a thiol (e.g. cysteine) on a biomolecule.

In embodiments, the first functional group LG comprises a leaving group, which leaves during reaction to reveal the reactive centre.

Preferably, the reactive centre of the first functional group LG undergoes reaction with a thiol moiety on the biomolecule.

In an embodiment, the first functional group LG is a halogen, e.g. a bromine atom, and the reactive centre is a carbocation.

In an embodiment, the first functional group LG is a chemical moiety suitable for use in enzyme-mediated labelling of biomolecules. Examples of said chemical moieties include, but are not limited to the following methods: Modified nucleotides for polymerase-directed labelling (See Holliger et al. Chem. Comm. 2009) or for terminal deoxynucleotidyl transferase-directed labelling (See Hollenstein et al ChemBiochem 2019); S-Adenosyl methionine derivatives for MTAse Labelling (See Deen, J. et al Angew Chem Int Ed 2016); Glycosyl donors, including glycosyl halides, glycan oxazoline and other glycosides, for glysosylation; Relevant enzymes include glycosidases, endoglycosynthases, glycosynthases, glycoceramidases or glycosyltransferases (See Wang etc al. Chem. Rev. 2018); Sortase substrates (eg. LPTXG) for Sortase A directed ligation (See Distefano et al. Chem. Rev. 2018); Q-Tags and K-Tags (e.g. LLQG) for Transglutaminase directed ligation (See Distefano et al Chem. Rev. 2018); Tyrosine and derivatives for Tyrosine ligase directed labelling (See Distefano et al Chem. Rev. 2018); Farnesyl diphosphate (FPP) derivatives for farnesyl transferase directed labelling (See Distefano et al Chem. Rev. 2018); Myristoyl-CoA derivatives for N-Myristoytransferase directed labelling (See Distefano et al Chem. Rev. 2018).

In a further preferred embodiment, the first functional group LG is a S-Adenosyl methionine derivative. In another preferred embodiment, the first functional group LG is a S-Adenosyl-I-homocysteine derivative.

It is to be understood that the second functional group FG and/or the first functional group LG may react with the label or biomolecule respectively by means of a chemical reaction (e.g. click chemistry) or a chemoenzymatic reaction (e.g. in an enzyme-mediated reaction). Any suitable functional group may be selected as FG and/or for LG for reaction, which is bio-orthogonal to the cleavable (e.g. hydrolysable) moiety A-B—C. For example, suitable reactions involving the first functional group LG or second functional group FG and the biomolecule and label respectively include click chemistry, cycloadditions, Staudinger reactions, epoxide ring opening reactions, nucleophilic substitutions, and/or nucleophilic additions.

Preferably, FG and LG are different types of functional group.

In a preferred embodiment, FG is an azide moiety and LG is an S-Adenosyl-L-homocysteine moiety. In another preferred embodiment, FG is an azide moiety and LG is a bromine moiety.

In embodiments, the linker molecule may have the following general formula:

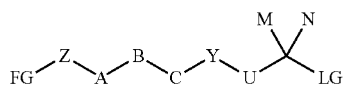

Wherein FG, Z, A-B—C, and LG are defined as above; and U represents an unsaturated bond selected from one of an alkene, an alkyne, an alkenyl, or aromatic group, a carbon atom comprising a carbonyl group, a sulphur atom comprising one or two S═O bonds; M and N independently represent a non-reactive group selected from one of a hydrogen atom, a deuterium atom, an aliphatic group, an aromatic group.

For example, M and N may both represent hydrogen atoms (or one or more deuterium atoms) to form a methylene (e.g. $CH_2$) linkage. Alternatively, one of M or N may represent an aliphatic or aromatic group to form a CHR linkage. Alternatively, both of M and N may represent an aliphatic or aromatic group ($R^1$, $R^2$) to form a $CR^1R^2$ linkage.

In embodiments, Z represents a non-reactive aliphatic linkage or an aromatic linkage comprising between 1 and 20 atoms (e.g. carbon atoms, oxygen atoms, and/or nitrogen atoms). The aliphatic and/or aromatic linkage may comprise a hydrocarbon backbone and/or a polyether backbone. Additionally or alternatively, Z may be an aromatic linkage comprising an aryl moiety, for example a $C_6H_4$ arene ring comprising two substituents, e.g. an ortho-, meta-, or para-substituted arene ring.

In embodiments, Z represents a polyether chain, e.g. a polyethylene glycol chain comprising up to 10 monomers of ethylene glycol, e.g. 9, 8, 7, 6, 5, 4, 3, 2, or 1 monomers of ethylene glycol. Additionally or alternatively, Z may comprise an aromatic group, e.g. a $C_6H_4(C{=}O)NH$ group.

For example, the linker molecule may have the following general structure:

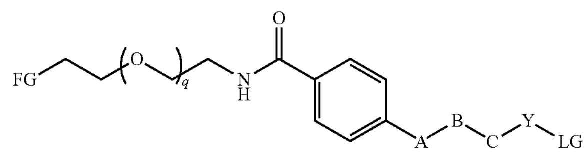

wherein FG, A-B—C, Y, and LG are defined as above; and q represents a number between 1 to 15, e.g. 1, 2, 3, 4, 5, 6, 7, 8, 9, 10, 11, 12, 13, 14, or 15; or a number between 1 to 10; or a number between 1 to 5, or a number between 1 to 4, or 1 to 3, or 1 to 2. In embodiments, q is 2 or 3.

For example, in embodiments, the linker molecule has the following general structure:

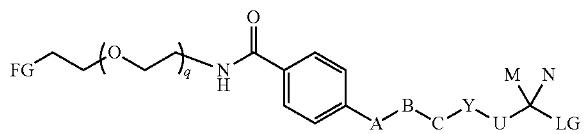

wherein FG, q, A-B—C, Y, U, M, N, and FG are defined as above or below.

In embodiments, the hydrolysable moiety is a Schiff base moiety. In embodiments the Schiff base moiety A-B—C represents one of the following moieties:

(i)

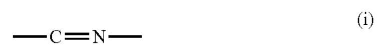

(ii)

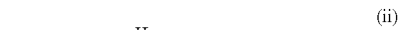

(iii)

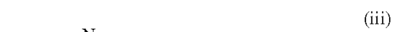

(iv)

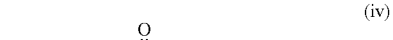

(v)

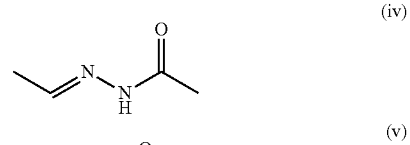

(vi)

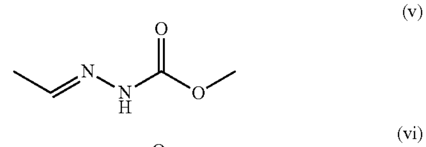

(vii)

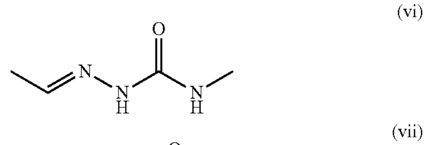

(viii)

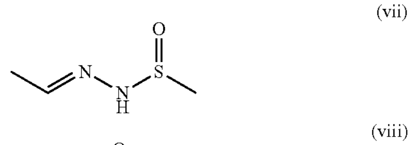

(ix)

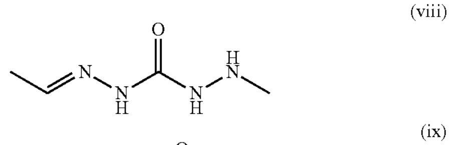

(x)

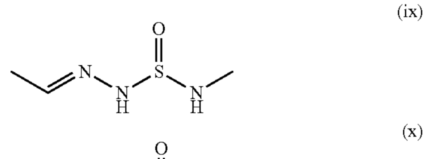

(xi)

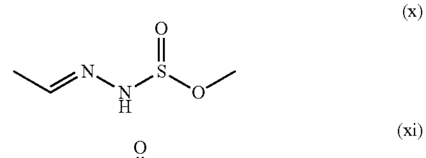

(xii)

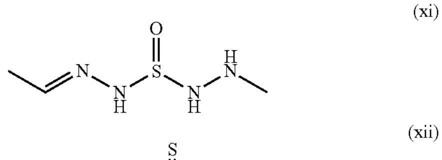

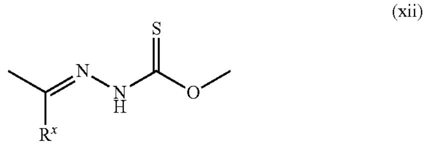

-continued (xiii)

(xiv)

(xv)

(xvi)

(xvii)

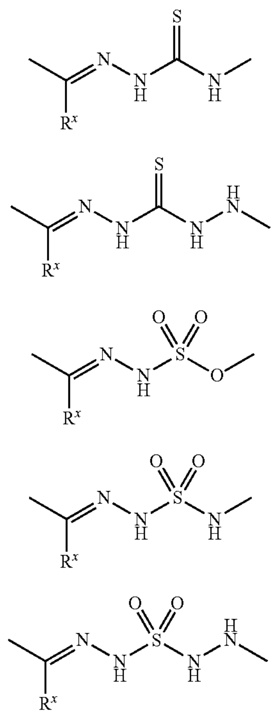

wherein $R^x$ represents one of a hydrogen atom, a deuterium atom, an aliphatic linkage, or an aromatic linkage.

In embodiments, Y represents a non-reactive aliphatic or aromatic chain, e.g. comprising between 1 and 15 atoms in the backbone, e.g. between 1 to 10, or 1 to 5 atoms in the backbone of the linker molecule. In embodiments, Y represents a non-reactive aliphatic or aromatic chain comprising between 1 to 15 $CH_2$ moieties, e.g. between 1 to 10 $CH_2$ moieties, or between 1 to 5 $CH_2$ moieties.

In embodiments, the third functional group is formed via hydrolysis of the hydrolysable moiety, e.g. Schiff bases described above, for example, using hydroxylamine. The third functional group may comprise an $NH_2$ moiety.

In a preferred embodiment, the Schiff base moiety is a N-substituted hydrazone or an O-substituted oxime.

In embodiments, the linker molecule has the following general formula:

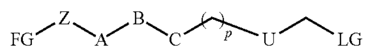

wherein p represents the number of $CH_2$ groups, p being between 1 to 15, e.g. 1, 2, 3, 4, 5, 6, 7, 8, 9, 10, 11, 12, 13, 14, or 15; or a number between 1 to 10; or a number between 1 to 5. In embodiments, p represents 4, that is Y represents $(CH_2)_4$.

In embodiments, U is an alkyne. In embodiments, the linker molecule has the following general formula:

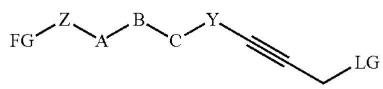

wherein FG, Z, A-B—C, Y, and LG are defined as above.

In alternative embodiments, U is an alkene. In embodiments, the linker molecule has the following general formula:

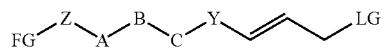

wherein FG, Z, A-B—C, Y, and LG are defined as above.

In embodiments, the biomolecule is a peptide, i.e. a polymer of amino acids. In embodiments, the peptide contains amino acids comprising a thiol moiety, e.g. a cysteine moiety.

In embodiments, the first functional group LG comprises a moiety that may act as a leaving group in a nucleophilic substitution reaction with a thiol moiety. In embodiments, LG is one of a halide (e.g. F, CL, Br, or I), a sulphonate (e.g. mesylate, tosylate), an iodonium salt, an acetate, an acrylate (e.g. methacrylate), an acrylamide (e.g. methacrylamide), maleimide (e.g. bromomaleimide, dibromomaleimide), bromopyridazinedione, propargylester, propagylamide, α-bromoester, α-bromoamide, 3-arylproiolonitrile, —$CH_2$-substituted trivalent sulphonium ion, an unsaturated bond (e.g. an alkene, an alkyne), an azide, an activated ester, and activated carbonate, a carbamate, an epoxide, an isothiocyanate, or an isocyanate moiety.

In embodiments, the linker molecule for labelling an amino acid and/or a peptide and/or a protein has the following general formula:

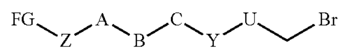

wherein FG represents the second functional group;

Z represents a non-reactive group selected from one of an aliphatic linkage or an aromatic linkage;

A-B—C represent the cleavable moiety, e.g. the hydrolysable moiety, e.g. the Schiff base moiety;

Y represents a non-reactive group selected from one of an aliphatic linkage or an aromatic linkage; and U represents an unsaturated bond selected from one of an alkene, an alkyne, an aryl group, a carbon atom comprising a carbonyl group, a sulphur atom comprising one or two S═O bonds.

In embodiments, U may represent an alkyne. In embodiments, the linker molecule may have the following general formula:

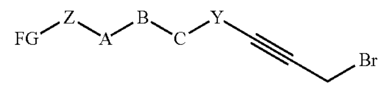

In alternative embodiments, U may represent an alkene. In embodiments, the linker molecule may have the following general formula:

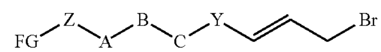

In embodiments, the linker molecule may have the following general formula:

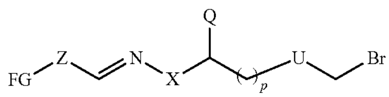

wherein the cleavable moiety, e.g. the hydrolysable moiety is a Schiff base moiety comprising the C═N—X—C-Q moiety;

U represents an unsaturated bond selected from one of an alkene, an alkyne, an aryl group, a carbon atom comprising a carbonyl group, a sulphur atom comprising one or two S═O bonds;

p represents a number between 1 to 15, e.g. 1, 2, 3, 4, 5, 6, 7, 8, 9, 10, 11, 12, 13, 14, or 15; or a number between 1 to 10; or a number between 1 to 5; e.g. p may be 4;

Q represents one of an oxygen atom or two hydrogen atoms or a deuterium atoms independently bonded to the carbon centre;

X represents one of an oxygen atom or a nitrogen atom;

Z represents a non-reactive group selected from one of an aliphatic linkage or an aromatic linkage;

FG represents the second functional group.

In embodiments, the linker molecule has the following general formula:

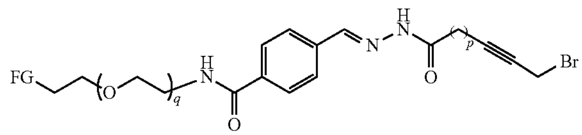

wherein the Schiff base moiety is the —C═N—N—C═O bond;

p represents a number between 1 to 15, e.g. 1, 2, 3, 4, 5, 6, 7, 8, 9, 10, 11, 12, 13, 14, or 15; or a number between 1 to 10; or a number between 1 to 5; e.g. p may be 4;

q represents a number between 1 to 15, e.g. 1, 2, 3, 4, 5, 6, 7, 8, 9, 10, 11, 12, 13, 14, or 15; or a number between 1 to 10; or a number between 1 to 5, or a number between 1 to 4, or 1 to 3, or 1 to 2; e.g. q may represent 2 or 3;

FG represents the second functional group.

In embodiments, the linker molecule has the following general formula:

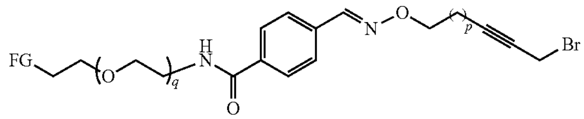

wherein the cleavable moiety, e.g. the hydrolysable moiety is a Schiff base moiety comprising the —C═N—O— bond;

p represents a number between 1 to 15, e.g. 1, 2, 3, 4, 5, 6, 7, 8, 9, 10, 11, 12, 13, 14, or 15; or a number between 1 to 10; or a number between 1 to 5; e.g. p may be 4;

q represents a number between 1 to 15, e.g. 1, 2, 3, 4, 5, 6, 7, 8, 9, 10, 11, 12, 13, 14, or 15; or a number between 1 to 10; or a number between 1 to 5, or a number between 1 to 4, or 1 to 3, or 1 to 2; e.g. q may be 2 or 3;

FG represents the second functional group.

In embodiments, the linker molecule has the following general formula:

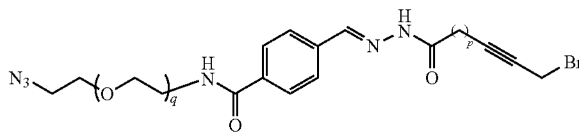

wherein p is 4 and q is 2 or 3.

In embodiments, the linker molecule has the following general formula:

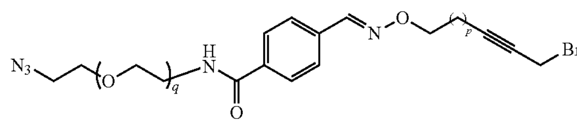

wherein p is 4 and q is 2 or 3.

In embodiments, the biomolecule is a polynucleotide, e.g. a strand of DNA or RNA.

In embodiments, the first functional group LG comprises a $CH_2$-substituted trivalent sulphonium ion comprising an R group, e.g. wherein the R group is represented by FG-Z-A-B—C—Y—U—$CH_2$—, which may be usable to form a covalent bond between the $CH_2$ group of the linker molecule and an atom of the biomolecule capable of alkylation. For example, the linker molecule may be a derivative of S-adenosyl-I-homocysteine, wherein LG is a S-Adenosyl-I-homocysteine. In this embodiment, the reactive centre of the first functional group LG is the carbon atom of the R group bonded to the sulphonium centre.

In embodiments, the linker molecule is a cofactor for use in an enzyme-mediated reaction. In embodiments, the linker molecule is an analogue of S-adenosyl-L-methionine cofactor.

In embodiments, step b. forming a covalent bond between the biomolecule and the first functional group may further comprise providing a catalyst, for example, an enzyme, e.g. a DNA methyltransferase enzyme capable of transferring an alkyl group from a S-adenosyl-I-methionine cofactor analogue.

In embodiments, the linker molecule has the following general formula:

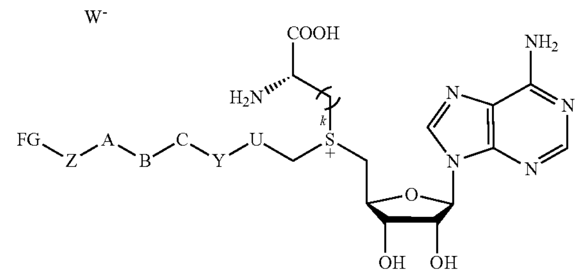

wherein FG represents the second functional group;

Z represents a non-reactive group selected from one of an aliphatic linkage or an aromatic linkage;

A-B—C represent the cleavable moiety, e.g. the hydrolysable moiety, e.g. the Schiff base moiety;

Y represents a non-reactive group selected from one of an aliphatic linkage or an aromatic linkage;

U represents an unsaturated bond selected from one of an alkene, an alkyne, an aryl group, a carbon atom comprising a carbonyl group, a sulphur atom comprising one or two S═O bonds;

k represents an integer of 1 or 2; and $W^-$ is a counter ion.

The counter ion $W^-$ may be one or more of a carbonate anion ($CO_3^{2-}$), a hydrogencarbonate ($HCO_3^-$), a tetrafluoroborate anion ($BF_4^-$), a hexafluorophosphate anion ($PF_6^-$), an acetate ($OAc^-$), a trifluoroacetate anion, a formate anion, halide (e.g. $F^-$, $Cl^-$, $Br^-$, $I^-$), or a sulphonate anion. The following embodiments comprise a sulphonium ion also comprise a counterion, although this is not shown.

Advantageously, the linker molecule may be used in a method according to the invention to write, erase, and rewrite polynucleotides. In the prior art, established and emerging approaches for studying deoxyribonucleic acid (DNA), ribonucleic acid (RNA) and proteins often rely on their conjugation with functional chemical groups, such as biotin or fluorophores. These functionalities enable manipulations from routine purification using immunoprecipitation to advanced analytical studies, such as fluorescence imaging. However, the current array of bioconjugation chemistries the methods employed for linking chemical functionality to biomolecule are largely inert. Hence, the conjugation focuses subsequent work towards a single application or analysis.

Methyltransferases (MTases) are emerging as important tool for the site-selective modification of DNA, RNA, and proteins. In nature, the methyltransferase enzyme catalyses the highly specific transfer of a methyl group from a S-adenosyl-1-methionine cofactor to DNA or RNA. The introduction of methyl groups to these classes of biomolecules helps to regulate gene expression levels within cells. This can either be through the modification of chromatin structure by the methylation of histones, or the direct methylation of DNA and RNA.

In mTAG labelling, a S-adenosyl-1-methionine cofactor analogue is employed wherein the methyl group is exchanged for a different moiety, e.g. a linker moiety or a label. The methyltransferase enzyme may then be used to alkylate the target biomolecule with the different moiety using the modified cofactor. By manipulating the chemical structure of the naturally occurring S-adenosyl-1-methionine cofactor, it is possible to use this labelling process as a method for the covalent introduction of functional groups to biomolecules. The linker moiety may comprise further functionality, which may be usable to further functionalise the biomolecule, e.g. with a label, tag, or a further biomolecule. One of the most common applications explored using this methodology sees the introduction of clickable groups to DNA for the introduction of fluorophores for mapping.

EP1712557 describes a method of labelling biopolymers using mTAG. It is shown that the reactivity of S-adenosyl-1-methionine cofactor analogues towards the transfer of extended saturated alkyl groups to the DNA biopolymer may be improved by adding an unsaturated carbon-carbon bond, e.g. an alkene, an alkyne, or an aromatic substituent, in the β-position to the sulfonium centre.

There have been several reports of methods of reversibly labelling polynucleotide biomolecules. For example, it is also known to use mTAG labelling followed by coupling with a cross-linking reagent comprising a cleavable disulphide bond using the redox reagent dithiothreitol (DTT). This allows for capture and release of DNA molecules for sequencing. However, disulphide chemistry has a number of drawbacks that limit its use in a biological system. For example, thiols are present in most biological samples and buffers. This leads to lower efficiencies of labelled biomolecules due to competing reactions. Moreover, disulphide chemistry cannot be applied to proteins because the oxidation state of cysteines often determines the 3D structure of the protein, and therefore a change in oxidation state leads to protein denaturation.

The method of the invention using the linker molecules described is bio-orthogonal.

Advantageously, the linker molecule according to embodiments of the invention comprising a trivalent sulphonium ion, comprises an unsaturated moiety U at a β-position to the sulphonium centre. This enhances the reactivity of the linker molecule to the alkylation of a polynucleotide biomolecule using a methyl transferase enzyme.

In embodiments, U may represent an alkyne. In embodiments, the linker molecule may have the following general formula:

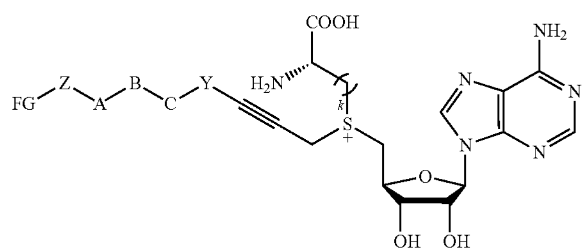

wherein FG, Z, A-B—C, Y, k are defined as above.

In alternative embodiments, U may represent an alkene. In embodiments, the linker molecule may have the following general formula:

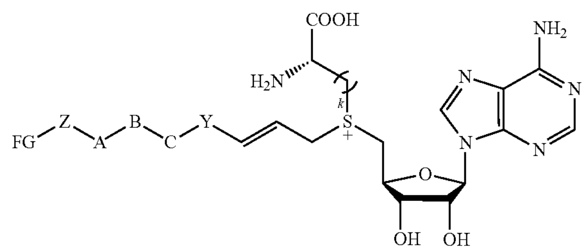

wherein FG, Z, A-B—C, Y, k are defined as above.

In embodiments, the linker molecule may have the following general formula:

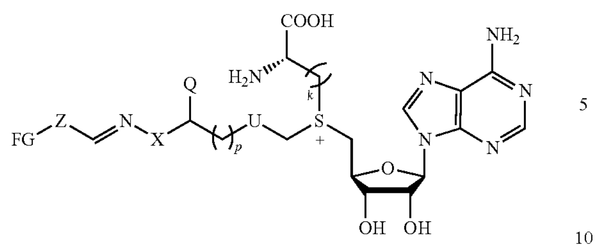

wherein the cleavable moiety, e.g. the hydrolysable moiety is a Schiff base moiety comprising the C═N—X—C-Q moiety;

p represents a number between 1 to 15, e.g. 1, 2, 3, 4, 5, 6, 7, 8, 9, 10, 11, 12, 13, 14, or 15; or a number between 1 to 10; or a number between 1 to 5; e.g. p may be 4;

Q represents one of an oxygen atom or two hydrogen atoms or a deuterium atoms independently bonded to the carbon centre;

U represents an unsaturated bond selected from one of an alkene, an alkyne, an aryl group, a carbon atom comprising a carbonyl group, a sulphur atom comprising one or two S═O bonds;

X represents one of an oxygen atom or a nitrogen atom;

Z represents a non-reactive group selected from one of an aliphatic linkage or an aromatic linkage;

k represents an integer of 1 or 2; and

FG represents the second functional group.

In embodiments, the linker molecule has the following general formula:

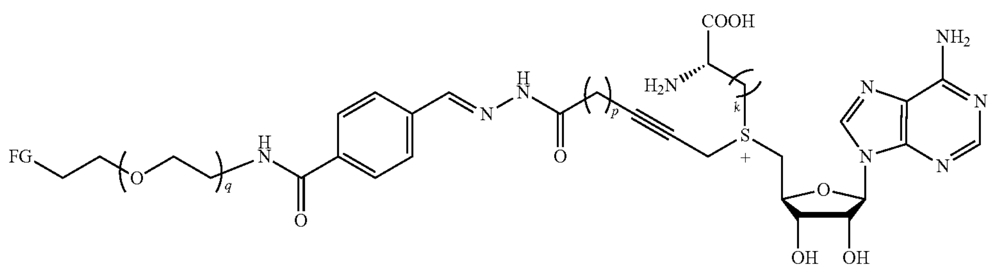

wherein the cleavable moiety, e.g. the hydrolysable moiety is a Schiff base moiety comprising the —C═N—N—C═O bond;

p represents a number between 1 to 15, e.g. 1, 2, 3, 4, 5, 6, 7, 8, 9, 10, 11, 12, 13, 14, or 15; or a number between 1 to 10; or a number between 1 to 5; e.g. p may be 4;

q represents a number between 1 to 15, e.g. 1, 2, 3, 4, 5, 6, 7, 8, 9, 10, 11, 12, 13, 14, or 15; or a number between 1 to 10; or a number between 1 to 5, or a number between 1 to 4, or 1 to 3, or 1 to 2; e.g. q may represent 2 or 3;

k represents an integer of 1 or 2; and

FG represents the second functional group.

In embodiments, the linker molecule has the following general formula:

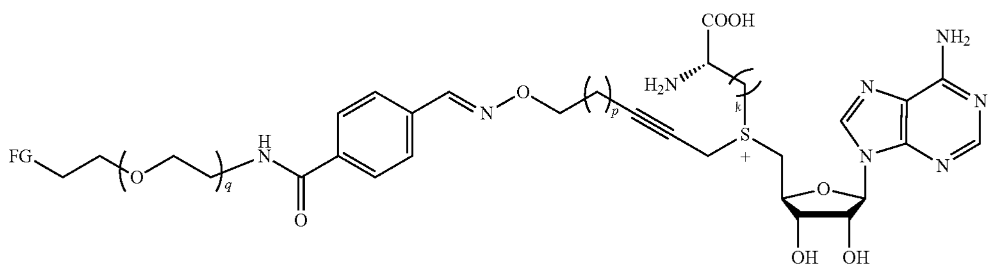

wherein the cleavable moiety, e.g. the hydrolysable moiety is a Schiff base moiety comprising the —C═N—O— bond;

p represents a number between 1 to 15, e.g. 1, 2, 3, 4, 5, 6, 7, 8, 9, 10, 11, 12, 13, 14, or 15; or a number between 1 to 10; or a number between 1 to 5; e.g. p may be 4;

wherein q represents a number between 1 to 15, e.g. 1, 2, 3, 4, 5, 6, 7, 8, 9, 10, 11, 12, 13, 14, or 15; or a number between 1 to 10; or a number between 1 to 5, or a number between 1 to 4, or 1 to 3, or 1 to 2; e.g. q may be 2 or 3;

k represents an integer of 1 or 2; and

FG represents the second functional group.

In embodiments, the linker molecule has the following general formula:

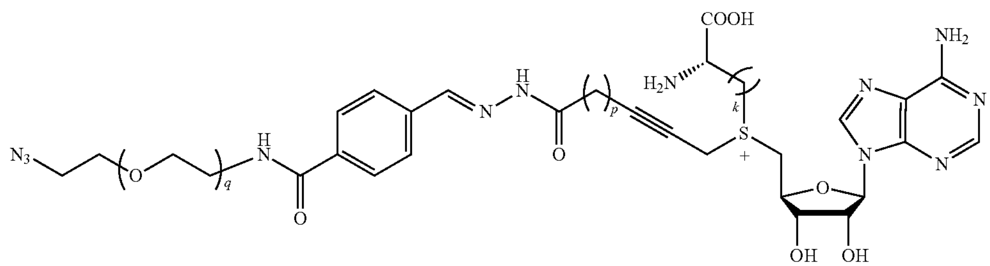

wherein p is 4 and q is 2 or 3; and k is defined as above.

In embodiments, the linker molecule has the following general formula:

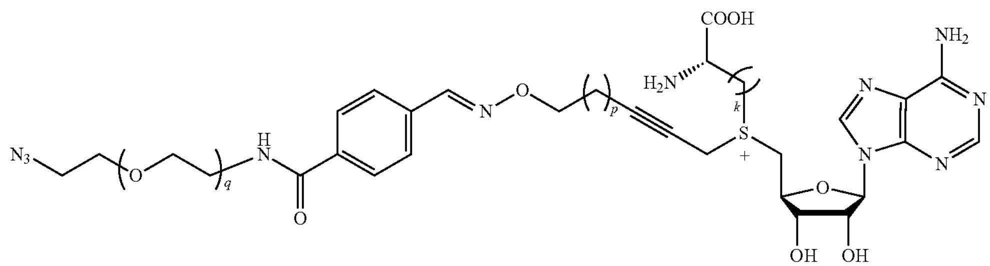

wherein p is 4 and q is 2 or 3; and k is defined as above.

In embodiments, wherein hydrolysing the cleavable moiety, e.g. the hydrolysable moiety, e.g. the Schiff base moiety, of the linker molecule to remove a label, e.g. the first label, or an $n^{th}$ label; and to form a third functional group may comprise treatment with hydroxylamine, for example in an ammonium acetate buffer solution, e.g. at pH 4.

In alternative embodiments, hydrolysing the Schiff base moiety may comprise heating the linker molecule and/or treatment with acid.

In the method of the invention, the reactive centre of the first functional group reacts with the biomolecule to form a covalent bond. The biomolecule comprises a functional group that is capable of reacting with the first functional group of the linker molecule to form a covalent bond. This may comprise a chemical reaction or an enzyme-mediated reaction. Advantageously, the first functional group of the linker molecule may be selected to react with a specific functional group on a specific biomolecule. In embodiments, the covalent bond formed between the biomolecule and the reactive centre of the first functional group may be, for example, a carbon-carbon bond, a carbon-nitrogen bond, a carbon-sulphur bond, or a carbon-oxygen bond.

In embodiments, the second and/or fourth functional group FG may be selected from one of a halide (e.g. an F, Cl, Br, or I atom), an unsaturated bond (e.g. an alkene, an alkyne), an azide, an activated ester, an activated carbonate, a carbamate, an epoxide, an isothiocyanate, or an isocyanate moiety. In the method of the invention, the reactive centre of the second functional group reacts with a first label to form a covalent bond. The first label comprises a functional group that is capable of reacting with the first functional group of the linker molecule to form a covalent bond. Advantageously, the second functional group of the linker molecule may be selected to react with a specific functional group on a specific label. In embodiments wherein the second functional group comprises, for example, an azide moiety, the functional group of the first, second, or $n^{th}$ linker may be an alkyne group, which is capable of reacting with the azide moiety via click chemistry. In embodiments, the covalent bond formed between the linker molecule and a label may be a carbon-nitrogen bond, e.g. formed from the reaction of an azide and an alkyne.

In embodiments, the one or more labels, e.g. the first label, a second label, and/or an $n^{th}$ label; may comprise one or more of a fluorescent molecule, a radioactive species, and/or a biological molecule such as biotin.

The third functional group is formed by hydrolysis of the hydrolysable moiety, e.g. the Schiff base moiety of the linker molecule. In embodiments, the third functional group comprise the $NH_2$ group of an O-substituted hydroxylamine moiety or an N-substituted hydrazone moiety.

The third functional group is usable in the method to reform the hydrolysable moiety, e.g. the Schiff base moiety, by reaction with a further molecule to form a covalent bond. In embodiments, the further molecule comprises an aldehyde moiety, which is capable of reaction with the third functional group, e.g. an $NH_2$ moiety, to reform the Schiff base. The covalent bond may comprise a carbon-nitrogen double bond, i.e. C═N.

In embodiments, the further molecule is represented by the following general formula:

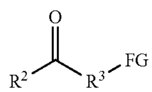

wherein $R^2$ represents one of a hydrogen atom, a deuterium atom, an aliphatic or an aromatic moiety, or a heteroatom (e.g. oxygen, nitrogen, sulphur);

$R^3$ represents one of an aliphatic moiety or an aromatic moiety;

FG represents the second functional group, for example, selected from one of an azide, an alkyne, an isothiocyanate, or an isocyanate moiety, or a label.

In embodiments, the further molecule is represented by the following general formula:

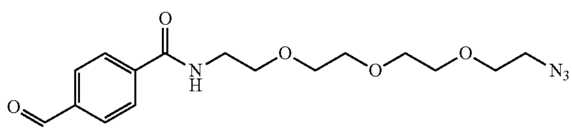

A further aspect of the invention provides a method of reversibly labelling a polynucleotide molecule, e.g. DNA, the method comprising:

a. providing a linker molecule (Compound A) having the following general formula:

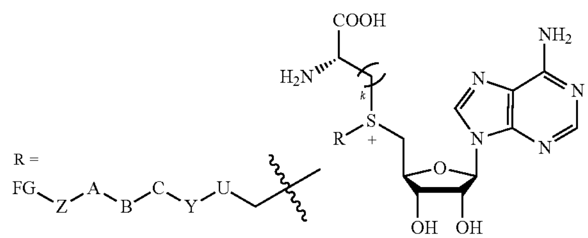

wherein R represents a transferable group;

FG represents the second functional group;

Z represents a non-reactive group selected from one of an aliphatic linkage or an aromatic linkage;

A-B—C represent the cleavable moiety, e.g. the hydrolysable moiety, e.g. a Schiff base moiety;

Y represents a non-reactive group selected from one of an aliphatic linkage or an aromatic linkage;

U represents an unsaturated bond selected from one of an alkene, an alkyne, an aryl group, a carbon atom comprising a carbonyl group, a sulphur atom comprising one or two S═O bonds;

k represents an integer of 1 or 2;

b. forming a covalent bond between the polynucleotide molecule and the R group of Compound A using a DNA methyltransferase enzyme which is capable of using Compound A as a cofactor and under conditions that allow for the transfer of the R group of Compound A onto the polynucleotide molecule;

c. forming a covalent bond between a first label and the second functional group FG of Compound A;

d. hydrolysing the cleavable moiety, e.g. the hydrolysable moiety, e.g. the Schiff base moiety, of the linker molecule to remove the first label and to form an O-substituted hydroxylamine or an N-substituted hydrazone;

e. forming a covalent bond between an aldehyde moiety of a further molecule and the O-substituted hydroxylamine or the N-substituted hydrazone to reform the Schiff base moiety.

A yet further aspect of the invention provides a method of reversibly labelling a polynucleotide molecule, e.g. DNA, the method comprising the following steps in the specified order:

a. incubating the polynucleotide molecule with Compound A in the presence of a methyl transferase enzyme which is capable of using Compound A as a cofactor and under conditions that allow for the transfer of the R group of Compound A onto the polynucleotide molecule to form an alkylated polynucleotide molecule "R-polynucleotide", wherein Compound A is represented by the following general formula;

Compound A

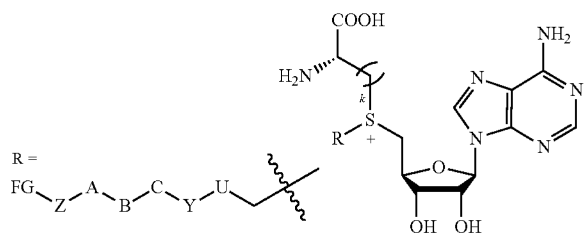

wherein FG represents the second functional group;

Z represents a non-reactive group selected from one of an aliphatic linkage or an aromatic linkage;

A-B—C represent a cleavable moiety, e.g. a hydrolysable moiety, e.g. a Schiff base moiety;

Y represents a non-reactive group selected from one of an aliphatic linkage or an aromatic linkage;

U represents an unsaturated bond selected from one of an alkene, an alkyne, an aryl group, a carbon atom comprising a carbonyl group, a sulphur atom comprising one or two S═0 bonds;

k represents an integer of 1 or 2;

b. incubating the alkylated polynucleotide molecule "R-polynucleotide" with a first label, the first label comprising a functional group that is capable of reacting with the functional group FG of the R group, to form a covalent bond between the "R-polynucleotide" and the first label, to form a first conjugate;

c. cleaving the cleavable moiety, e.g. the hydrolysable moiety, e.g. the Schiff base moiety, of the first conjugate to remove the first label;

d. reactivating the cleavable moiety, e.g. the hydrolysable moiety, e.g. the Schiff base moiety to re-form the "R-polynucleotide";

e. incubating the "R-polynucleotide" with a second label, the second label comprising a functional group that is capable of reacting with the functional group FG of the R group, to form a covalent bond between the "R-polynucleotide" and the second label, to form a second conjugate.

In embodiments, the method may further comprise cleaving the Schiff base moiety of the second conjugate to remove the second label.

Advantageously, the method according to the invention is bio-orthogonal, that is, it may be performed in a biological system without interfering with the native biochemical processes. More advantageously, once reversed, the modification made to a polynucleotide biomolecule, e.g. DNA, is relatively small and hydrophilic meaning it will not affect the way DNA interacts in solution or with enzymes.

The linker molecule comprises a cleavable moiety, e.g. a hydrolysable moiety, e.g. the Schiff base moiety, which is cleavable or hydrolysable such that a label may be reversibly conjugated to the biomolecule. Advantageously, the conditions required to cleave or hydrolyse the cleavable or hydrolysable moiety, e.g. the Schiff base moiety are mild, which does not damage the structure of the biomolecule. Interestingly, Schiff base chemistry is not commonly found in biomolecules, unlike prior art approaches such as the use of disulphide linkages. More advantageously, hydrolysable moieties such as oximes and hydrazones are stable at physiological pH.

The covalent bonds formed using the linker molecule are reversible and rewritable. Advantageously, the label molecule may be used for repeated modifications of biomolecules, for example, labelling, capture, release, refunctionalisation for, e.g. fluorescent labelling, and/or imaging.

The analogue of S-adenosyl-1-methionine cofactor may be designed to comprise a linker molecule of any suitable structure.

Advantageously, the second functional group of the linker molecule is usable to further functionalise the biomolecule, e.g. polynucleotide, for example using click chemistry. This may be used for DNA capture, DNA complexation, drug attachment, and/or fluorescent labelling.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. For the avoidance of doubt, the terms "may", "and/or", "e.g.", "for example" and any similar term as used herein should be interpreted as non-limiting such that any feature so-described need not be present. Indeed, any combination of optional features is expressly envisaged without departing from the scope of the invention, whether or not these are expressly claimed. The applicant reserves the right to change any originally filed claim or file any new claim accordingly, including the right to amend any originally filed claim to depend from and/or incorporate any feature of any other claim although not originally claimed in that manner.

BRIEF DESCRIPTION OF THE DRAWINGS

Embodiments of the invention will now be described by way of example only with reference to the accompanying drawings in which.

DETAILED DESCRIPTION OF THE PREFERRED EMBODIMENTS

Figure 1:
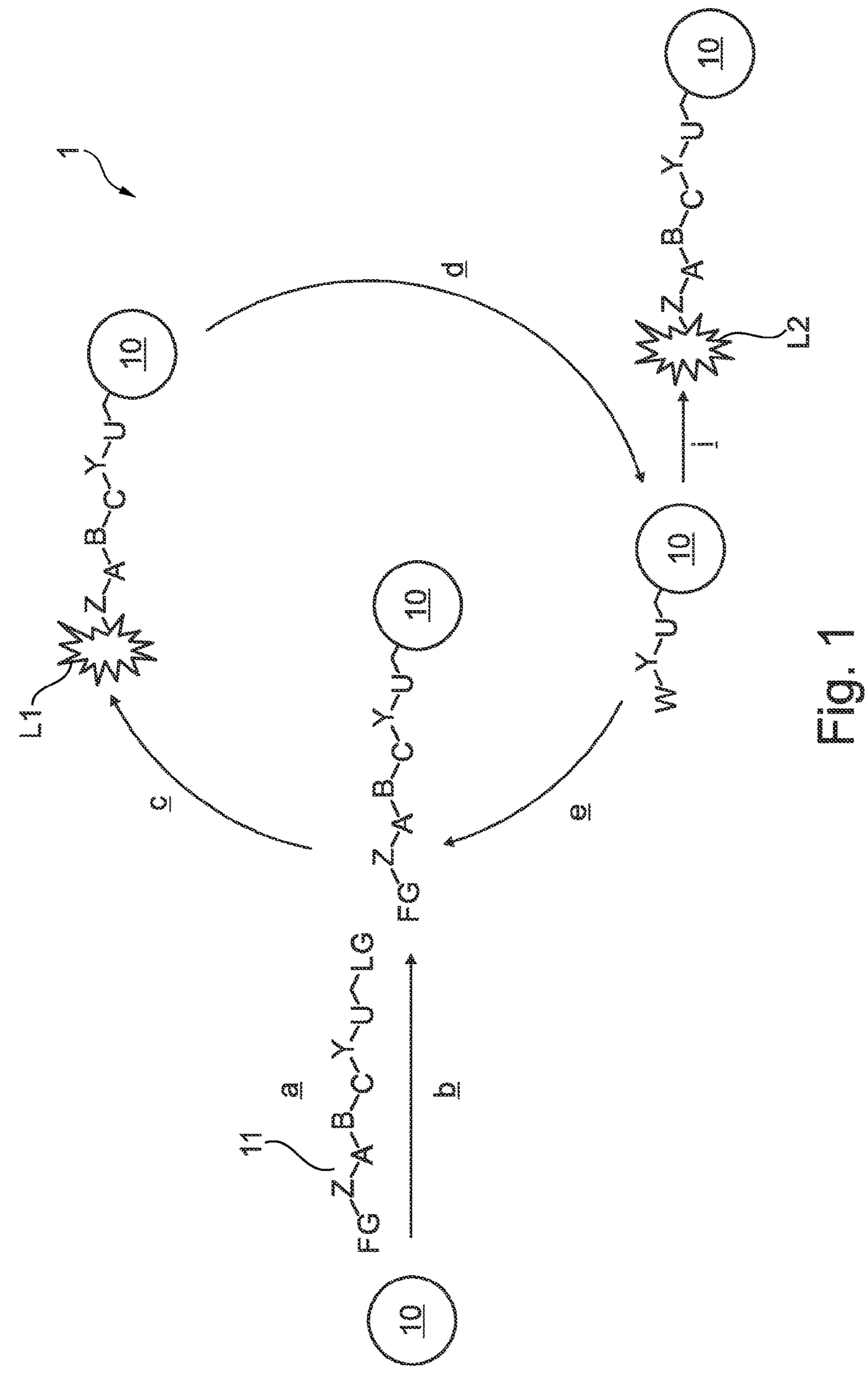
FIG. 1 is a schematic representation of the reversible and rewritable modification of a biomolecule according to an embodiment of the invention.

Referring now to FIG. 1, there is shown a schematic representation 1 of the reversible and rewritable modification of biomolecule 10 according to an embodiment of the invention.

There is shown a biomolecule 10 and a linker molecule 11. The linker molecule ii comprises a first functional group LG comprising a reactive centre, a second functional group FG comprising a reactive centre, a hydrolysable moiety (e.g. a Schiff base moiety) A-B—C, non-reactive groups Y and Z, and an unsaturated bond U. There is also shown a first label L1 and a second label L2.

The method of reversibly labelling the biomolecule 10 comprises the following steps, which are labelled on the schematic representation:

a) providing a linker molecule 11, the linker molecule 11 comprising a first functional group LG comprising a reactive centre, a second functional group FG comprising a reactive centre, and a hydrolysable moiety, e.g. a Schiff base moiety, A-B—C;

b) forming a covalent bond between the biomolecule 10 and the reactive centre of the first functional group LG;

c) forming a covalent bond between the first label L1 and the reactive centre of the second functional group FG;

d) hydrolysing the hydrolysable moiety A-B—C of the linker molecule 11 to remove the first label L1 and to form a third functional group W comprising a reactive centre;

e) forming a covalent bond between a further molecule (not shown) and the reactive centre of the third functional group W to reform the hydrolysable moiety A-B—C.

Advantageously, the covalent bond formed between the reactive centre of the first functional group LG of linker molecule 11 and the biomolecule 10 adds chemical functionality to the biomolecule 10 in the form of the further functional group FG and the hydrolysable moiety A-B—C.

The method of the invention may further comprise the optional step i. of forming a covalent bond between a further molecule comprising a label, e.g. the second label L2, and the reactive centre of the third functional group W, to reform the hydrolysable moiety A-B—C.

In embodiments, step c. may be performed before step b.

Figure 2A:
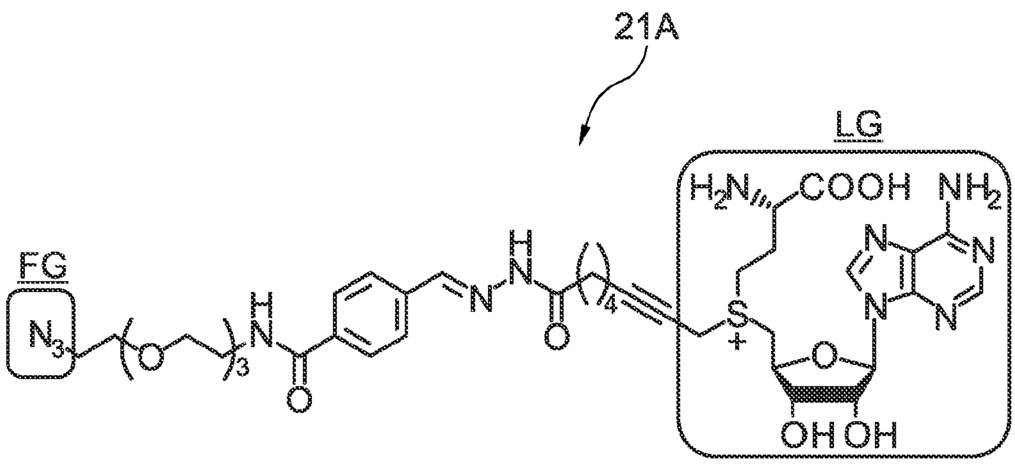
FIG. 2A is a schematic representation of linker molecules according to an embodiment of the invention.
Figure 2A:
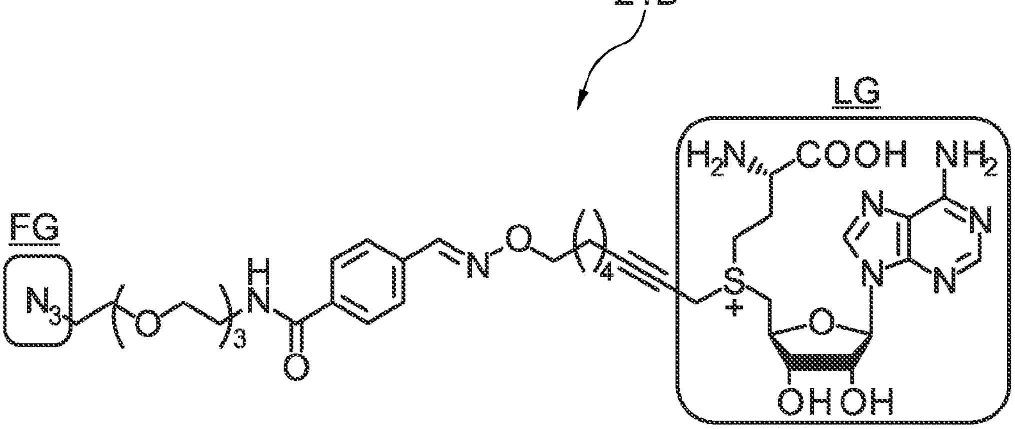
Figure 2A:
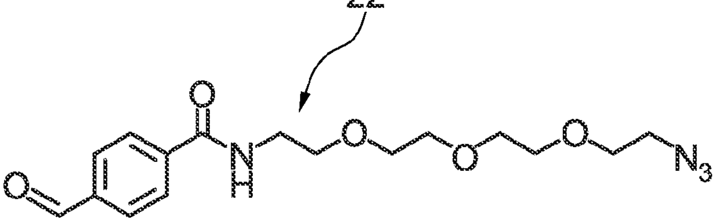

Referring first to FIG. 2A, there is shown two linker molecule structures; 21A and 21B.

Figure 2B:
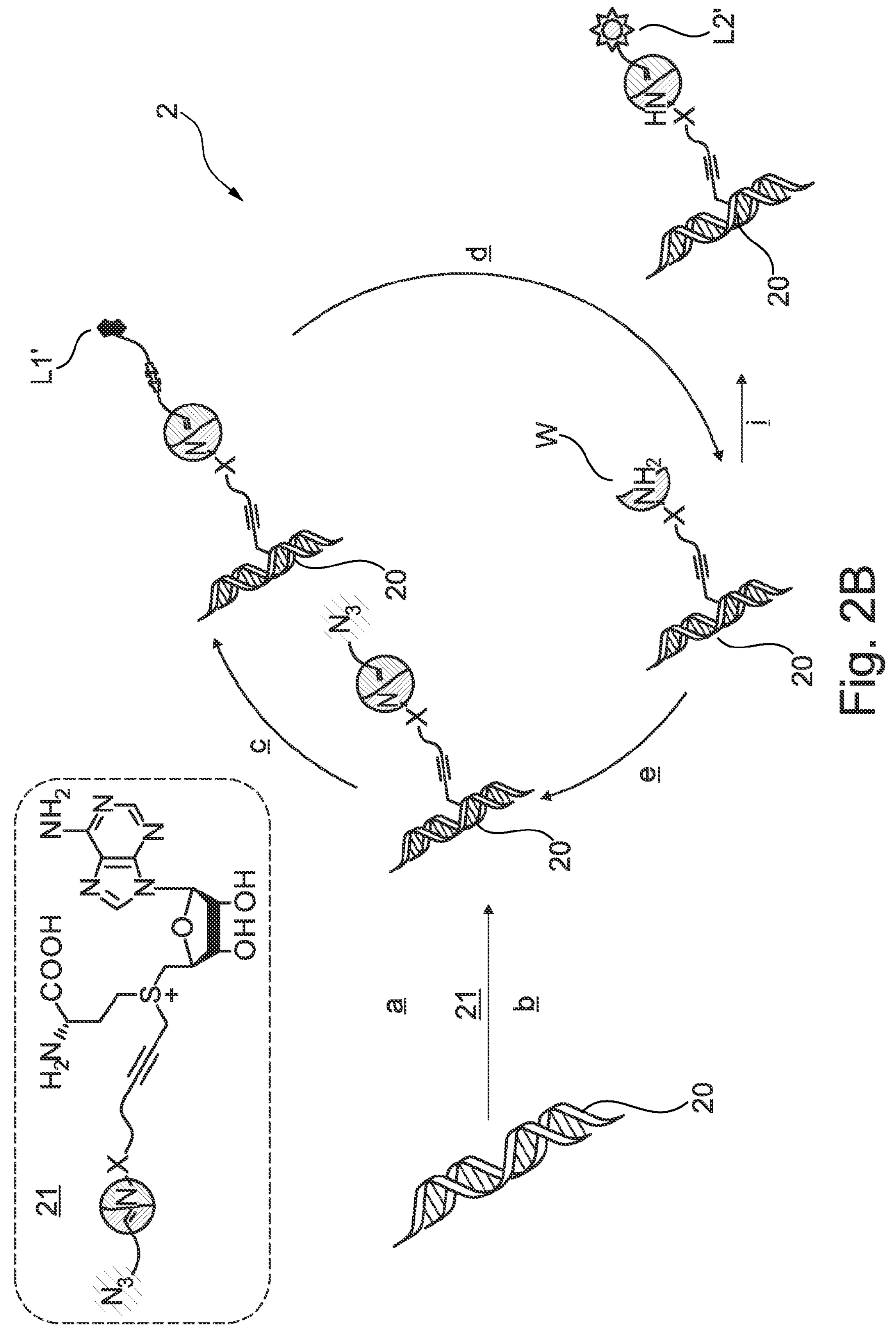
FIG. 2B is a schematic representation of the reversible and rewritable modification of a biomolecule according to a further embodiment of the invention.

Referring also to FIG. 2B, there is shown a schematic representation 2 of the reversible and rewritable modification of biomolecule 20, according to a further embodiment of the invention.

There is shown a biomolecule 20 and the linker molecule 21. The linker molecule 21 may be either of those shown in FIG. 2A. The linker molecules 21A, 21B each comprise a first functional group LG, a second functional group FG, and a hydrolysable moiety A-B—C.

There is also shown a first label L1' and a second label L2'.

In this embodiment, the biomolecule 20 is a DNA molecule and the linker molecule 21 is an analogue of the S-adenosyl-1-methionine cofactor.

The first functional group LG of the linker molecule 21A, 21B is S-adenosyl-I-homocysteine, the second functional group FG of the linker molecule is an azide moiety, the hydrolysable moiety is one of an hydrazone (Linker 21A) or an oxime (Linker 21B).

In this embodiment, hydrolysis of the hydrolysable moiety (e.g. Schiff base) A-B—C further comprises treatment with hydroxylamine, for example in an ammonium acetate buffer solution, e.g. at pH 4. The hydrolysable moiety A-B—C is hydrolysed to provide a third functional group W comprising a reactive centre; an N-substituted hydrazone (wherein the Schiff base is a hydroxylamine) or an O-substituted hydroxylamine (wherein the Schiff base is an oxime).

The further molecule 22 for use in step e. to form a covalent bond with the $NH_2$ group of the N-substituted hydrazone (21A) or an O-substituted hydroxylamine (21B) to reform the hydrazone (21A) or the oxime (21B) Schiff base moiety is also shown in FIG. 2A.

In this embodiment, the functional group of the first label L1' and the second label L2' are both an alkyne moiety, which forms a C—N covalent bond with the reactive centre of the second functional group FG (an azide moiety) via a click chemistry reaction.

In this embodiment, step b. of the method 2 further comprises providing a catalyst, for example, an enzyme, e.g. a DNA methyltransferase enzyme capable of transferring an alkyl group from a S-adenosyl-1-methionine cofactor analogue.

The reversible and rewritable modification of DNA molecule 20 comprises the following steps, which are labelled on the schematic representation:

a) providing a linker molecule 21A or 21B
   the linker molecule 21A or 21B comprising a S-Adenosyl-I-homocysteine moiety comprising a $CH_2$-substituted trivalent sulphonium ion moiety LG, an azide moiety FG, and a hydrazone (21A) or an oxime (21B) or Schiff base moiety A-B—C;

b) site-selective MTase-directed writing of DNA molecule 20
   forming a covalent bond between the DNA molecule 20 (on one or more of a cytosine C5, cytosine N4 or adenosine N6) and the carbon of the $CH_2$ group of the linker molecule 21A or 21B;

c) modification of DNA molecule 20 via azide-alkyne cycloaddition
   forming a C—N covalent bond between the alkyne moiety of the first label L1' and the azide of the linker molecule 21A or 21B;

d) erasing introduced functionality via dynamic exchange
   hydrolysing the hydrazone (21A) or oxime (21B) Schiff base moiety of the linker molecule 21A or 21B to form N-substituted hydrazone (21A) or an O-substituted hydroxylamine (21B).

e) re-writing the intermediate DNA molecule via Schiff-base formation
   forming a covalent bond between a further molecule (not shown) and the $NH_2$ group of the N-substituted hydrazone (21A) or an O-substituted hydroxylamine (21B) to reform the hydrazone (21A) or the oxime (21B) Schiff base moiety.

Optionally, Step i. may involve further functionalising the DNA intermediate via standard conjugation techniques.

The further molecule, e.g. that of step e. or that of step i.; comprises an aldehyde moiety for reaction with the $NH_2$ functionality of the third functional group to reform the Schiff base.

To further exemplify the invention, reference is also made to the following non-limiting Examples:

Synthesis of Precursor 1 for Use in the Synthesis of Linker 21A

Figure 3:
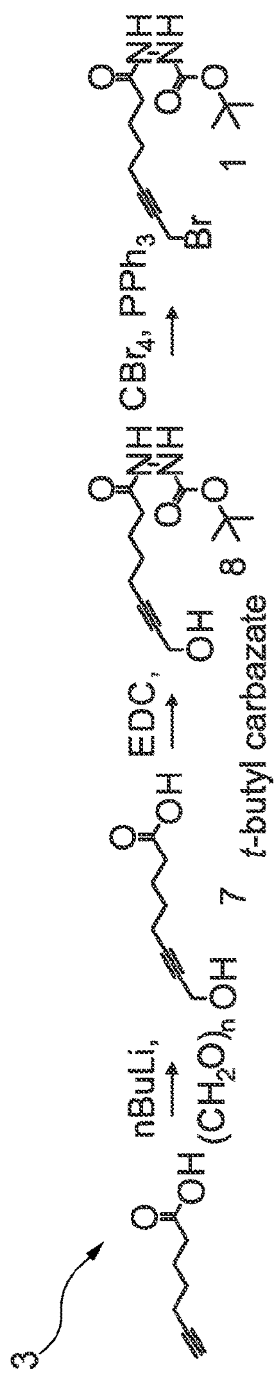
FIG. 3 is a reaction scheme for the formation of a precursor to the linker molecule containing a hydrazone Schiff base 21A.

Referring now to FIG. 3, there is shown a reaction scheme for the formation of a precursor 1 to the linker molecule containing a hydrazone Schiff base 21A. The precursor 1 was synthesised using the following protocol.

1.1 Synthesis of 8-hydroxyoct-6-ynoic acid 7

A solution of 6-heptynoic acid (2 g, 15.87 mmol) was made in dry THF (42 ml) under argon, to this HMPA (34.9 mmol, 6.13 ml) was added and the solution was cooled to −78° C. To this nBuLi (1.6 M in hexanes, 34.9 mmol, 21.8 ml) was added dropwise whilst maintaining the temperature below −60° C. The solution was then warmed to −40° C. and stirred for 1 hour. After 1 hour paraformaldehyde (1.47 g, 47.6 mmol) was added via powder funnel under an argon flow. The reaction mixture was then warmed to 45° C. for 4 hours. After reaction, the mixture was quenched with 1 M HCl to pH 4-5 and extracted with EtOAc. The solvent was then dried and the EtOAc was removed by rotary evaporation giving the crude product. Purification was completed using flash column chromatography (silica gel, Hex:EtOAc, 6:4): Yield=68%, Rf=0.27 (Hex:EtOAc, 6:4); $^1$H NMR (300 MHz, DMSO-d6) δ 12.03 (s, 1H), 5.03 (s, 1H), 4.02 (d, J=2.6 Hz, 2H), 2.29-2.14 (m, 4H), 1.63-1.50 (m, 2H), 1.50-1.39 (m, 2H); MS: m/z [M−H]=155.46.

1.2 Synthesis of tert-butyl 2-(8-hydroxyoct-6-ynoyl)hydrazine-1-carboxylate 8

8-hydroxyoct-6-ynoic acid 7 (1.35 g, 8.65 mmol) and tert-butyl carbazate (1.4 g, 10.38 mmol) were dissolved in 2:1 THF:H2O (13.5:6.75 ml). To this EDC·HCl (1.87 g, 9.52 mmol) was added slowly over 15 minutes. The mixture was left to stir for 3 hours and then extracted with EtOAc. The organic layer was washed with 0.1 M HCl, water and brine and then the organic layer is collected, dried over anhydrous sodium sulfate and the and the solvent was removed under reduced pressure yielding the product as a white solid: Yield=63%; $^1$H NMR (400 MHz, DMSO-d6) δ 9.47 (s, 1H), 8.66 (s, 1H), 5.04 (t, J=5.9 Hz, 1H), 4.02 (dt, J=5.9, 2.2 Hz, 2H), 2.19 (tt, J=7.1, 2.2 Hz, 2H), 2.06 (t, J=7.2 Hz, 2H), 1.58 (p, J=7.3 Hz, 2H), 1.50-1.32 (m, 12H); $^{13}$C NMR (101 MHz, DMSO) δ 172.01, 84.36, 80.94, 79.42, 49.59, 33.06, 28.53, 28.08, 24.70, 18.24; MS: m/z [M+Na]=294.15.

1.3 Synthesis of tert-butyl 2-(8-bromooct-6-ynoyl)hydrazine-1-carboxylate 1

A solution of tert-butyl 2-(8-hydroxyoct-6-ynoyl)hydrazine-1-carboxylate 8 (300 mg, 1.11 mmol) was made in dry DCM (3.33 ml) and cooled on ice. Triphenylphosphine (437 mg, 1.67 mmol) was added and left to dissolve, once dissolved tetrabromomethane (552 mg, 1.67 mmol) was added slowly. The reaction was then brought to room temperature and left to stir for 1 hour. After reaction the solvent was removed under reduced pressure and the crude mixture was purified by flash column chromatography (silica gel Hex:EtOAc, 7:3): Yield=55%; Rf=0.15 (Hex: EtOAc 7:3); $^1$H NMR (300 MHz, DMSO-d6) δ 9.48 (s, $^1$H), 8.67 (s, 1H), 4.21 (t, J=2.3 Hz, 2H), 2.27 (tt, J=6.9, 3.4 Hz, 2H), 2.06 (t, J=7.4 Hz, 2H), 1.65-1.31 (m, 13H); $^{13}$C NMR (101 MHz, DMSO) δ 171.4, 155.2, 87.7, 78.9, 76.3, 54.9, 39.5, 32.5, 28.0, 27.3, 24.1, 17.9, 17.2; MS: m/z [M+Na] =355/357.08.

Synthesis of Precursor 4 for Use in the Synthesis of Linker 21B

Figure 4:
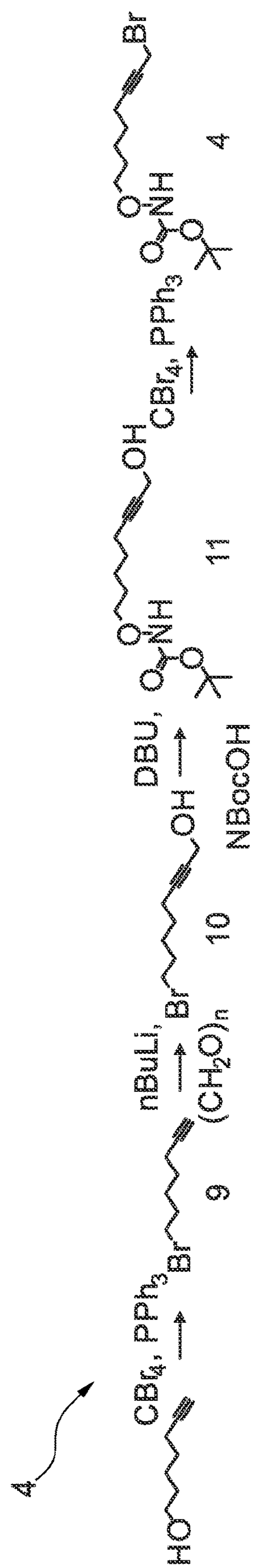
FIG. 4 is a reaction scheme for the formation of a precursor to the linker molecule containing an oxime Schiff base 21B.

Referring now to FIG. 4, there is shown a reaction scheme for the formation of a precursor 4 to the linker molecule containing an oxime Schiff base 21B. The precursor 4 was synthesised using the following protocol.

2.1 Synthesis of 7-Bromo-hept-1-yne 9

A solution of 6-heptyn-1-ol (5 g, 44.6 mmol) was made in dry DCM (60 ml) and cooled on ice. To this triphenylphosphine (17.6 g, 67 mmol) was added, upon complete dissolution tetrabromomethane (22.2 g, 67 mmol) was added slowly. The reaction mixture was brought to room temperature and stirred for 1 hr. After completion, the solvent was removed under reduced pressure. Hexane was added to the crude forming a white suspension. The hexanefraction was filtered, collected and then the solvent was removed. An oily residue remained which was purified by flash column chromatography with hexane: Yield=91%, Rf=0.45 (hexane); %); vmax(neat)/cm-1 540 (C—Br); $^1$H NMR (300 MHz, DMSO-d6) δ 3.53 (t, J=6.7 Hz, 2H), 2.75 (t, J=2.7 Hz, 1H), 2.23-2.10 (m, 2H), 1.89-1.74 (m, 2H), 1.50-1.43 (m, 4H).

2.2 Synthesis of 8-bromooct-2-yn-1-ol 10

A solution of 7-bromohept-1-yne 9 (20.56 mmol, 3600 mg) was made in Dry THF (12.3 ml) and cooled to −78° C. under Argon. To this a solution of nBuLi in hexanes (1.6 M, 13 ml) was added dropwise, whilst maintaining the temperature below −60° C. The reaction mixture was then warmed to 0° C. in an ice bath at which point paraformaldehyde (1718 mg, 55.5 mmol) was added under a flow of Argon and stirred for 30 minutes. The mixture was then warmed to room temperature and left to stir, the temperature was maintained below 30° C. until the exothermic reaction had stopped. The mixture was then heated to 45° C. for 2 hrs. Once complete the reaction was extracted with ether and sat. $NH_4Cl$. The organic layer was collected and the solvents were removed under reduced pressure to yield the crude product as an oil. Once dry, purification was completed by flash column chromatography (silica gel, Hexane: Ethyl Acetate, 9:1). The product was then collected as a colourless oil: Yield=55%, Rf=0.15 (Hex: EtOAc 9:1), $^1$H NMR (300 MHz, DMSO-d6) δ 5.04 (t, J=5.7 Hz, 1H), 4.03 (dt, J=5.5, 2.1 Hz, 2H), 3.54 (t, J=6.7 Hz, 2H), 2.20 (m, 2H), 1.88-1.75 (m, 2H), 1.52-1.40 (m, 4H).

2.3 Synthesis of tert-butyl ((8-hydroxyoct-6-yn-1-yl)oxy)carbamate 11

To a solution of N-Boc Hydroxyl amine (890 mg, 6.55 mmol) in DMF (4.3 ml) 8-bromooct-2-yn-1-ol (10) (1200 mg, 5.85 mmol) and 1,8-Diazabicyclo[5.4.0]undec-7-ene (1000 mg, 6.55 mmol) was added. The solution was stirred at 50° C. for 20 hrs. Once complete, the reaction was extracted with DCM and 15% citric acid solution. The organic phases were dried and collected and the solvent was removed under reduced pressure. A colourless oil was collected as the crude product. This was further purified by flash column chromatography (silica gel, Hexane: Ethyl Acetate, 8:2). The product was collected as a colourless oil: Yield=73%, Rf=0.27; $^1$H NMR (300 MHz, DMSO-d6) δ 9.91 (s, 1H), 5.03 (t, J=5.9 Hz, 1H), 4.02 (dt, J=5.9, 2.2 Hz, 2H), 3.66 (t, J=6.2 Hz, 2H), 2.17 (tt, J=6.7, 1.7 Hz, 2H), 1.40 (m, 15H); MS: m/z [M+H]=258.2.

2.4 Synthesis of tert-butyl ((8-bromooct-6-yn-1-yl)oxy)carbamate 4

A solution of tert-butyl((8-hydroxyoct-6-yn-1-yl)oxy)carbamate 11 (1 g, 3.89 mmol) was made in dry DCM (5.2 ml) and cooled on ice. To this triphenylphosphine (1.53 g, 67 mmol) was added. Upon complete dissolution tetrabromomethane (1.94 g, 67 mmol) was added slowly. The reaction mixture was brought to room temperature and allowed to stir for 1 hr. After completion, the solvent was removed under reduced pressure. Purification was completed using flash column chromatography (silica gel, Hexane: Ethyl Acetate, 8:2): Yield=67%, Rf 0.52 (Hex: EtOAc, 8:2); vmax(neat)/cm-1 1712 (C═O), 607 (C—Br); $^1$H NMR (300 MHz, DMSO-d6) δ 9.90 (s, 1H), 4.21 (t, J=2.4 Hz, 2H), 3.66 (t, J=6.2 Hz, 2H), 2.25 (tt, J=6.9, 2.4 Hz, 2H), 1.40 (m, 15H); $^{13}$C NMR (101 MHz, DMSO) δ 156.04, 87.85, 79.37, 76.22, 75.05, 39.52, 28.05, 27.64, 27.04, 24.76, 18.06, 17.25; MS: m/z [M+Na]=342.35/344.35, [M-$^t$BuOH]=246.38/248.38.

Figure 5:
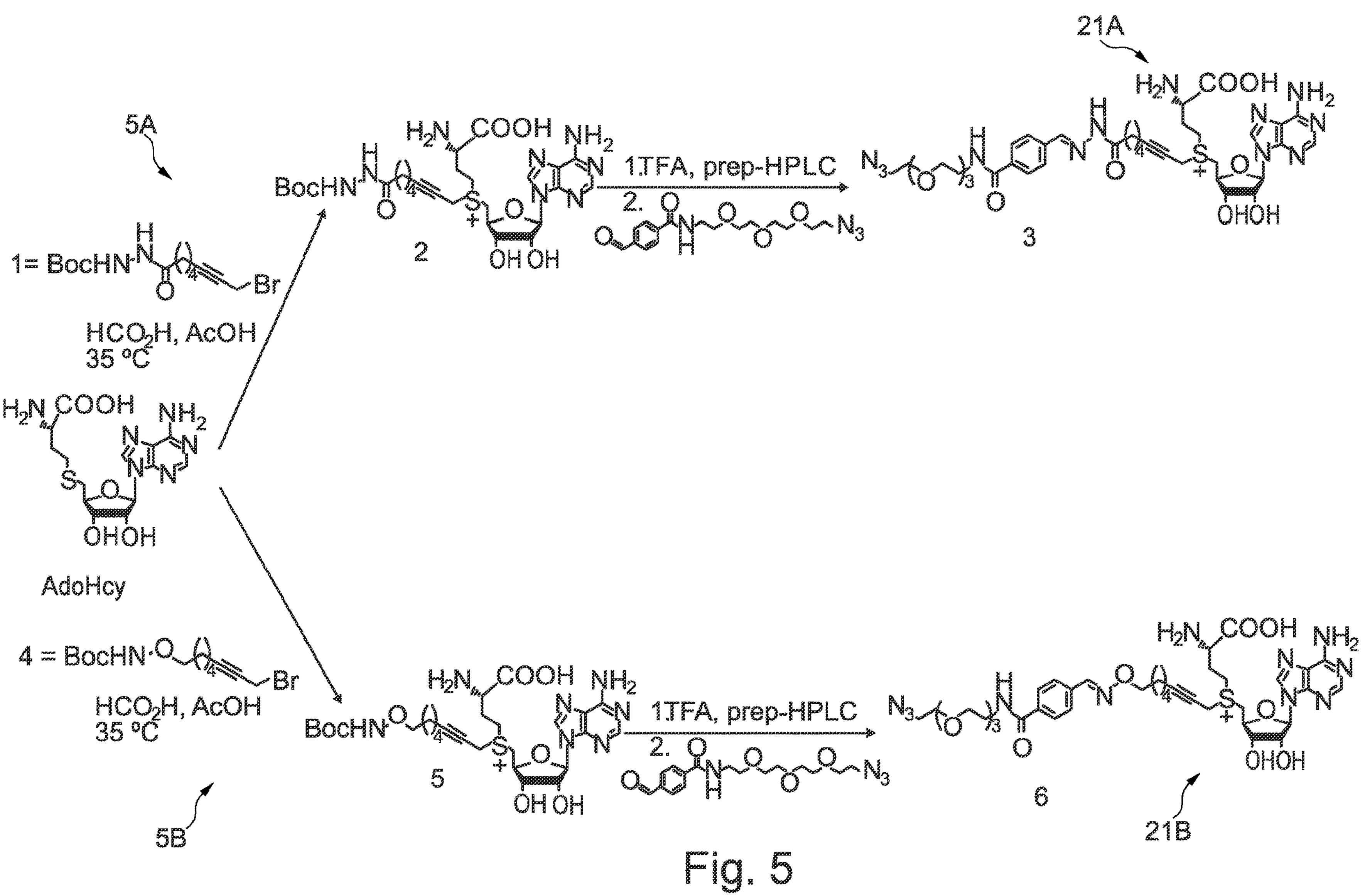
FIG. 5 is a reaction scheme for the formation of S-adenosyl-1-methionine cofactor analogues.

Example of a Linker Molecule for the Enzymatic Labelling of a Polynucleotide: MTase-Directed Labelling of a Polynucleotide Synthesis of Linker Molecules 21A, 21B Referring now to FIG. 5, there is shown a reaction scheme 5A for the formation the linker molecule containing a hydrazone Schiff base 21A from precursor 1. There is also shown a reaction scheme 5B for the formation the linker molecule containing an oxime Schiff base 21B from precursor 4.

3) Synthesis of S-adenosyl-1-methionine Cofactor Analogues 21A, 21B 3.1 General coupling procedure Precursors 1, 4 were prepared and reacted with S-adenosyl-L-homocysteine under acidic conditions to give reversible and rewritable Boc-protected AdoMet derivatives.

A solution of S-adenosyl-1-homocysteine (15 mg, 0.04 mmol) was made in a 1:1 mixture of formic and acetic acid (300 μl). Precursor 1 or 4 (tert-butyl 2-(8-bromooct-6-ynoyl) hydrazone-1-carboxylate or tert-butyl ((8-bromooct-6-yn-1-yl)oxy)carbamate) (1.2 mmol, 30 equivs) was then added dropwise, on ice. The reaction mixture was warmed to 35° C. and left to stir overnight. After overnight stirring the reaction mixture was extracted with diethyl ether and the aqueous layer was collected and dried by lyophilisation: MS: m/z [M+H]=638 (2), [M+H]=624 (5).

3.2 Cofactor Deprotection

The AdoMet analogues were deprotected under acidic conditions to reveal the hydrazone or alkoxyamine moieties.

The crude product was dissolved in TFA (400 μl) and left stir for 2 hrs at room temperature. After reaction the acid was removed under a flow of argon.

3.3 Cofactor Purification

Any excess precursor was removed by purification.

Both diastereomers of the deprotected cofactors could be separated by HPLC, a separation which was not possible at later stages.

The crude reaction mixture was then dissolved in water (2 ml). Purification of AdoMet analogues was performed by preparative reversed-phase HPLC (ACE 5 C-18 25×2.12 cm) eluting with 20 mM Ammonium Acetate pH 5.5 Water (A)/MeOH (B) gradient at a flow rate of 10 ml/min. Gradient system: 30 mins 3-30% B, 30-97% B over 30 mins, hold at 97% B for 5 minutes, stop programme. Retention times: Hydrazide iso. 1=17.51 mins, iso. 2=18.73 mins, hydroxylamine iso. 1=25.47 mins, iso. 2=28.24 mins: MS: m/z [M+H]=538 (2), [M+H]=524 (5).

The deprotected AdoMet derivatives slowly degrade, in particular following freeze-drying, via multiple pathways, giving additional peaks at higher retention times.

3.4 Aldehyde coupling

To mitigate against degradation the AdoMet derivatives were reacted with a commercially available benzaldehyde immediately after purification by HPLC in order to minimise side reactions due to the nucleophilic nature of the hydrazone and alkoxyamine moieties.

To the collected HPLC fractions Ald-PEG3-N3 (1.2 equivs) was added and rolled for 30 mins at room temperature. The fractions were then dried by lyophilisation. Once dry the solids were dissolved in 100 μl 0.1% Acetic Acid and stored at −20° C. Concentrations were determined by UV absorption analysis with E260=15.400 $dm^{-3}$ $mol^{-1}$ $cm^{-1}$: MS: m/z [M+H]=867 (3), [M+H]=856 (6).

The resulting linker molecules 21A and 21B contain reactive terminal azides that can be readily conjugated to a range if functional groups, while condensation of the aldehyde with the hydrazone or alkoxyamine incorporates a dynamic functionality, that can be reversibly functionalised.

A slight excess of aldehyde (1.2 equivs) was employed to ensure full functionalisation of the deprotected intermediate.

No degradation of the freeze-dried AdoMet derivatives 21A and 21B was observed.

MTase-Directed Labelling of a Polynucleotide with 21A and 21B

A restriction assay was used to demonstrate the activity of the MTases with the linker molecules 21A and 21B.

Figure 6A:
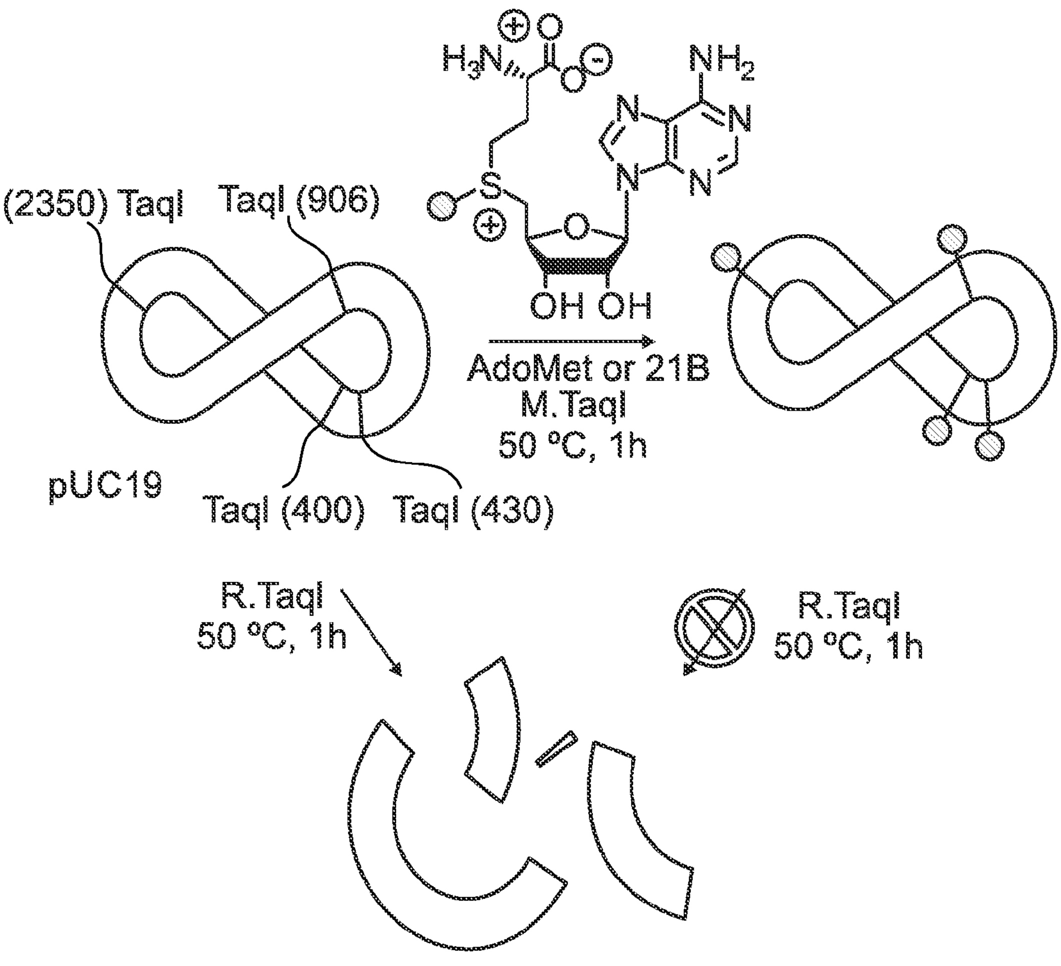
FIG. 6A is a schematic representation of a restriction assay.

M.TaqI (an N6-adenine DNA MTase) was incubated at 50° C. for 1 hour with a linker molecule 21A, 21B and plasmid pUC19, which has four recognition sites (TCGA) for the enzyme, see FIG. 6A.

Successful transfer of the functional group by M.TaqI results in protection of the plasmid from restriction digestion by R.TaqI, an endonuclease with the same target site as M.TaqI.

Referring now to FIG. 7B, there is shown gel electrophoresis of pUC19 following enzymatic treatment with M.TaqI and/or R.TaqI in the presence or absence of AdoMet (375 μl) or linker 21B.

Figure 6B:
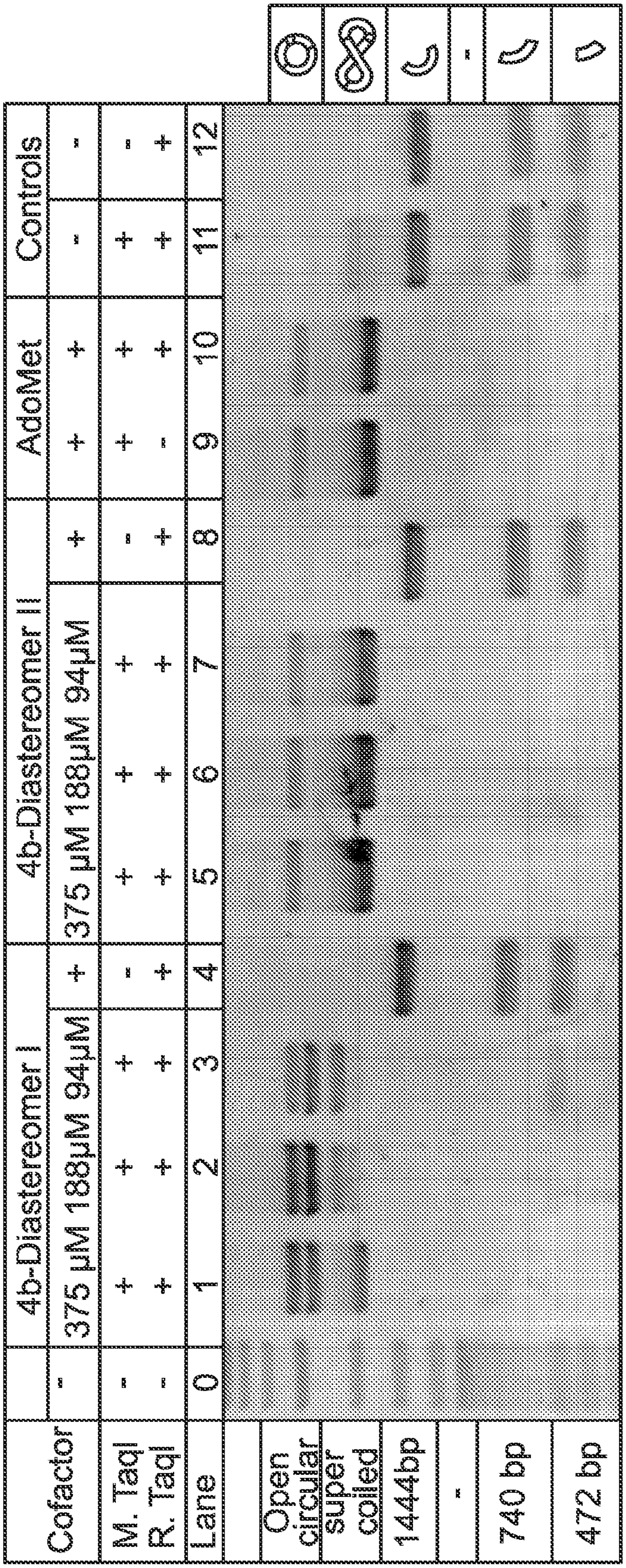
FIG. 6B displays analysis of enzymatic DNA labelling by gel electrophoresis.

In the absence of M.TaqI-mediated alkylation (FIG. 6B, lanes 4, 8 and 12), pUC19 is cut into fragments, of which the largest three can be identified by gel electrophoresis. M.TaqI-mediated alkylation with AdoMet (FIG. 6B, lane 10) or linker 21B (FIG. 6B, lanes 1-3 and 5-7) results in partial to full protection from restriction by R.TaqI, with mainly open circular and supercoiled plasmid DNA being observed by gel electrophoresis. Neither isomer interferes with the ability of R.TaqI to digest plasmid DNA (FIG. 6B, lanes 4 and 8).

Controls were run in the absence of AdoMet (FIG. 6B, lanes 11 and 12), in the absence of M.TaqI (FIG. 6B, lanes 4, 8 and 12) and in the absence of R.TaqI (FIG. 6B, lane 9) and showed labelling to be successful.

To test the labelling efficiency of each isomer, a cofactor dilution series was run to highlight any differences in affinity with the enzyme, with the second fraction having higher activity. The preferential isomer, diastereomer II, was carried forward for future experiments. Similar effects were seen with linker 21A. Both linker molecules 21A and 21B have the potential to be employed for the dynamic labelling of biomolecules.

M.MpeI is a cytosine-C5 MTase which targets the CpG dinucleotide. pUC19 was incubated with mutant M.MpeI (Q136A, N347A) and linker 21B before restriction enzyme R.HaeII, which targets a subset of the CpG dinucleotides, was added. Efficient transalkylation of plasmid DNA with M.MpeI was also observed.

Evidence of the ability of MTases to alkylate DNA with linker 21A, 21B was achieved by targeting a 14 base pair oligonucleotide with one copy of M.TaqI sequence (TCGA) for transalkylation. Labelling of the oligo was monitored directly using HPLC. Analysis was performed above the melting temperature of the DNA so that both strands could be clearly identified in the chromatogram. A clear shift in the retention time was seen upon labelling with linker 21A, 21B when compared to the retention times of the unmodified DNA. The shift was observed for both peaks, demonstrating that M.TaqI was able to label both strands as a consequence of the palindromic nature of the sequence MTase recognizes. The shift was proportional to the size and nature of the linker transferred, with the AdoMet methylation resulting in a small shift in retention time and the oxime derivate 21B giving the biggest shift. The presence of a small amount of erased oligo DNA was observed and is likely due to hydrolysis under the HPLC conditions. Analysis of the individual peaks was carried out using MS which confirmed labelling was successful and the nature of the sidechain functionality introduced following incubation.

Reversible Enzymatic Labelling Protocol

The following protocols may be used in accordance with the embodiment shown in FIGS. 2A and 2B.

1) Enzymatic Labelling (Step b of Method of the Invention)

For each sample a solution of oligo biomolecule (120 μl, 10 μM), buffer (40 μl, 10×NEB cutsmart buffer), M.TaqI (45 μl), water (189 μl) and linker molecule (6 μl, 20 mM) was made. Samples were incubated at 50° C. for 1.5 hrs. After incubation proteinase K (2.5 μl) was added and the samples were incubated at 50° C. for a further 1 hr. The samples were then purified using the Qiagen® Qiaquick nucleotide clean up kit and eluted into 50 μl water and their concentration was measured by shimadzu biospec-nano. Samples not to be reversed were taken and stored in the fridge until HPLC analysis.

2) Schiff Base Reversal (Step c of Method of the Invention)

To the hydrazone labelled DNA, a solution of $H_2NOH{\cdot}HCl$ in water (10 μl, 10 equivs) was added. The pH of the solution was then adjusted using 100 mM Ammonium Acetate Buffer (pH 4.0, 7 μl). The samples were then incubated at 50° C. for 1.5 hrs and then stored in the fridge until analysis.

3) HPLC Labelling Analysis

Purification of labelled oligonucleotides was performed by analytical reversed-phase HPLC (Phenomenex, Gemini, 5 μm, C18, 110 Å) eluting with a 0.1 M Triethyl amine acetate buffer, pH 7.0 (A)/MeCN (B) gradient, at a flow rate of 1 ml/min 60° C. Gradient system A: 5-18% B over 25 mins, to 100% 5 mins, hold at 100% 10 mins, lower to 5% for 5 mins. System B: 5-31% B over 50 mins, to 100% 10 mins, hold at 100% 5 mins, lower to 5% for 10 mins. For unlabelled and methylated oligonucleotides gradient A was used and for all remaining samples system B was used. Fractions were collected and analysed by mass spectrometry.

Under these conditions the hydrazone labelled oligo DNA melts and both DNA strands can be observed independently. Over 85% of the functional linker was cleaved with the new HPLC peak shifted to lower retention time, following the loss of the potentially hydrophobic aldehyde.

The oxime labelled oligo DNA under these conditions remains intact, consistent with the higher stability of this type of Schiff base.

4) Rewriting the Original Functionality Via Schiff Base Formation

Figure 7:
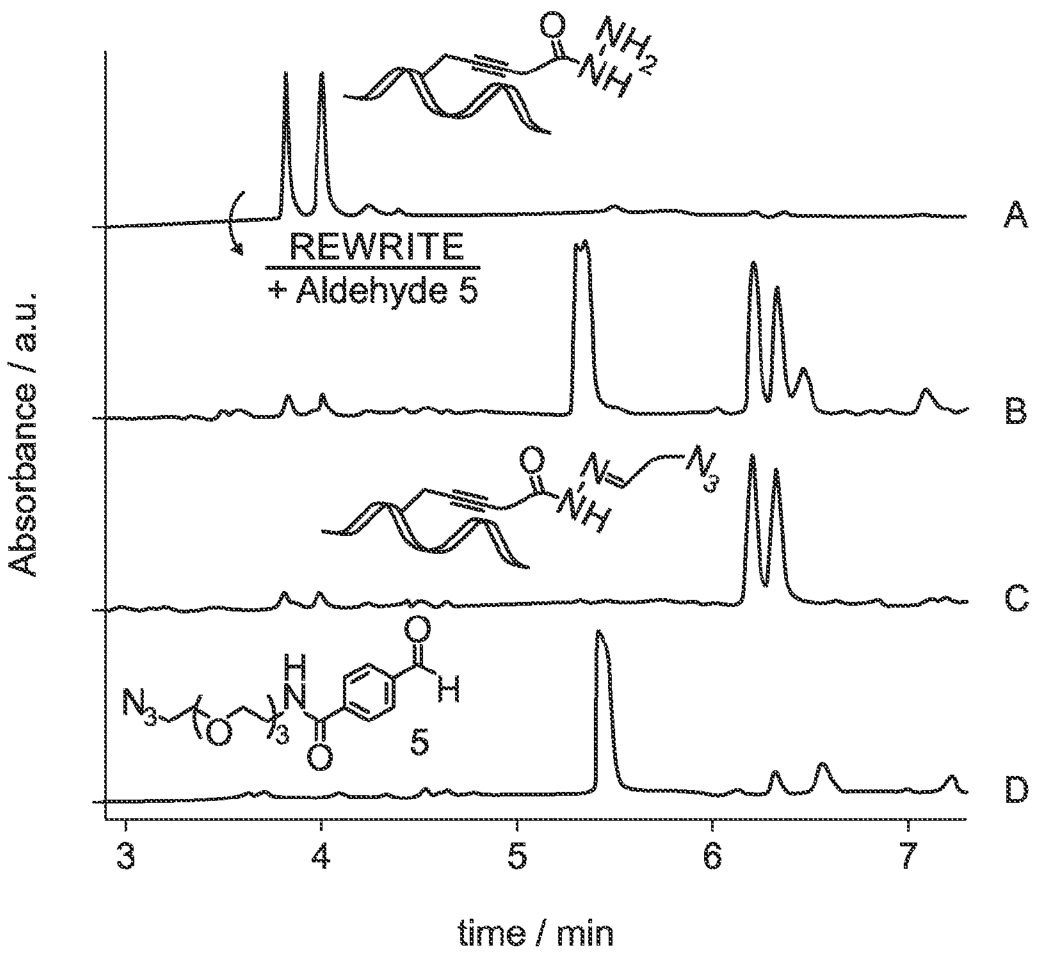
FIG. 7 displays analytical HPLC chromatographs following rewriting the original functionality of DNA.

The hydrazide functionalized oligo DNA (FIG. 7, line A) was incubated in the presence of an excess of aldehyde 5 (FIG. 7). A clear shift in the retention time of the main peaks associated with oligo DNA was observed (FIG. 7, line B). Chromatographs obtained following incubation of oligo DNA with M.TaqI and linker 21A (FIG. 7, line C) show good overlap of the peaks associated with azide-functionalized DNA at ~6.2 and 6.4 mins, and a similar ratio of this peak to that of the free hydrazide (at 3.8 and 4.0 mins). The presence of a small amount of hydrazide functionalized oligo DNA is likely due to hydrolysis of the Schiff base under the HPLC conditions. Three additional peaks were observed following rewriting with aldehyde, which overlapped with those observed when this aldehyde was incubated with $H_2NOH·HCl$ (FIG. 7, line D). Analysis of the individual peaks was carried out by LC-MS which confirmed rewriting was successful and the nature of the chemical functionality on the oligo DNA.

5) Further Modification Following Schiff-Base Cleavage.

Fragments of DNA generated by PCR, containing 17 CpG sites, were site-selectively labelled with M.MpeI. Labelling was followed by incubation with $H_2NOH·HCl$ and reaction with a commercially available NHS-activated fluorophore Atto647N (further funtionalisation). The reaction was monitored via gel electrophoresis and shows specific conjugation of Atto647N to DNA modified with linker 21B. While no red-fluorescence was observed in the absence of Atto647N, this dye is positively charged and was able to non-specifically associate with the DNA in the control samples. Comparison of the intensities of the red and green (Sybr® Green) channels, to evaluate the degree of labelling with Atto647N per unit DNA showed a degree of labelling 4.8 times higher for the DNA that has undergone the write-erase than in the absence of the erase step, $H_2NOH·HCl$ treatment, and over 23 times higher than in the absence of the write step, MTase directed labelling.

6) Dual Modification

Figure 8:
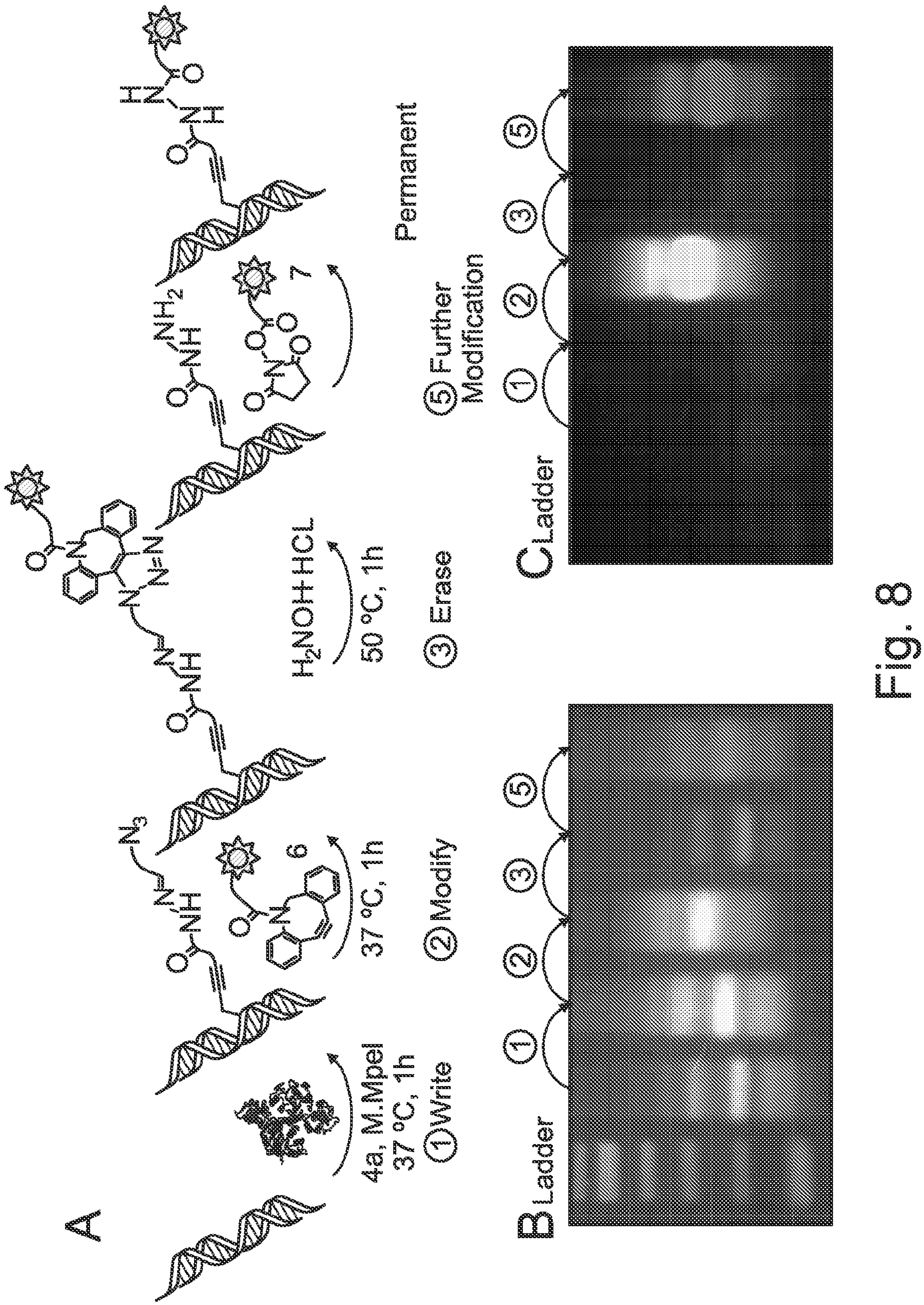
FIG. 8 is a schematic representation of the dual functionalisation of DNA.

Sequential modification with complementary fluorescent dyes was achieved by labelling short DNA fragments with two different fluorescent dyes (write-modify-erase-further modification). To this end, DNA fragments were first incubated with M.MpeI and dynamic linker 21A, to yield azide-functionalized DNA (FIG. 8, image A, Step 1). This modification resulted in a small shift in the migration time of the DNA on gel (FIG. 8, image B, Step 2) but, as expected, no fluorescence was observed (FIG. 8, image C, Step 1). A further shift in the migration time was observed when the azide-functionalized DNA was modified with TAMRA-DBCO 6 (FIG. 8, image B, Step 2) but, more importantly, emission from DNA-associated TAMRA fluorophore was clearly observed (FIG. 8, image, C, Step 2). Erasing the TAMRA modification was achieved by incubation with an excess of $H_2NOH·HCl$. No fluorescence was observed from the resulting DNA fragments (FIG. 8, image C, Step 3) and a shift back to the original migration time was observed (FIG. 8, image B, Step 3), suggesting that this hydrazide linker had little impact on the physical properties of the DNA. Incubation of this hydrazide-functionalized DNA with NHS-activated Atto647N 7 resulted in a new shift in migration time (FIG. 8, image B, Step 4) and corresponding appearance of fluorescence, now visible under red illumination (FIG. 8, image C, Step 4).

Modification was monitored using gel electrophoresis: DNA concentration; 7 ng/μL, release buffer; 10 mM Ammonium Acetate, pH 6.8, 1 M NaCl, 0.01% SDS. DNA stained with GelRed®. Gel was visualized using a Bio-Rad Pharos FX (GelRed®: excitation, trans-UV; emission filter, 590/110 nm; TAMRA: excitation, epi-green illumination; emission filter: 602/50 nm; Atto 647N 7: excitation, epi-red illumination; emission filter: 700/50 nm). TAMRA channel was colored yellow and Atto 647N 7 was coloured red for visualization. (B) GelRed® channel and (C) Composite image of TAMRA and Atto647n channels.

Figure 9:
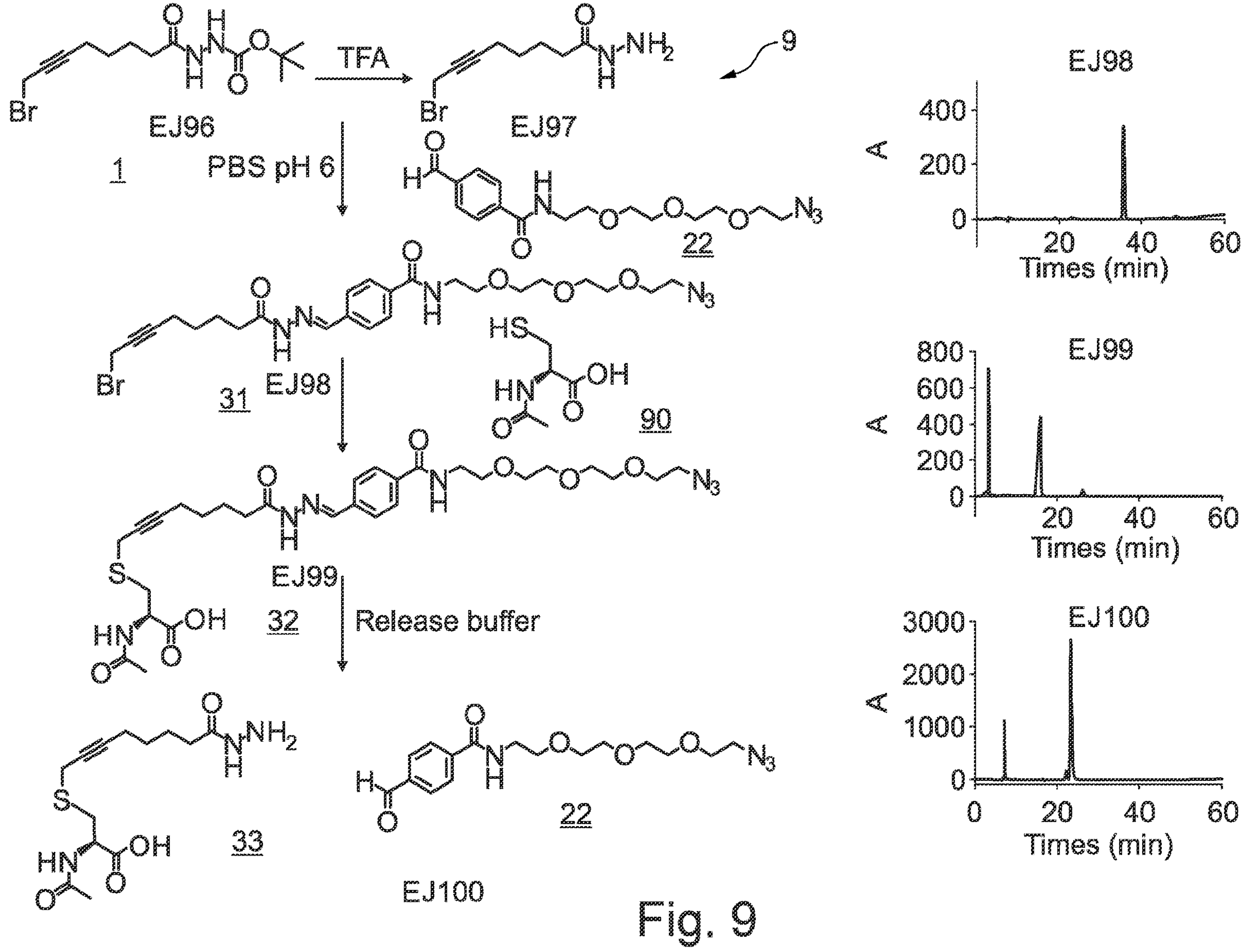
FIG. 9 is a reaction scheme for the formation of a further linker molecule.

Example of the Chemical Labelling of a Biomolecule: Cysteine Labelling of a Peptide Referring now to FIG. 9, there is shown a synthetic route to a further linker molecule 31 using Precursor 1 as described in FIG. 3, wherein the first functional group LG is a bromine atom.

Synthesis of N-(2-(2-(2-(2-azidoethoxy)ethoxy)ethoxy)ethyl)-4-((2-(8-bromooct-6-ynoyl)hydrazoneylidene)methyl)benzamide 31

Activated linker (tert-butyl 2-(8-bromooct-6-ynoyl)hydrazone-1-carboxylate) 1 (20 mg, 0.06 mmol) was dissolved in 500 μL of TFA and stirred for 2 hours. TFA was evaporated to afford 14 mg of a yellow oil. This crude was then dissolved in 200 μL of PBS and Ald-Ph-PEG-Azide (22) (21 mg, 1 eq.) in solution in PBS was added (pH 7). Instantly, a white precipitate appeared. This white solid was filtered and dissolved in DCM for purification by HPLC preparative (0-60% ACN 40 min). MS: m/z [M+Na]=586.8/588.8 to afford linker molecule 31.

1) Chemical Labelling an Amino Acid (Step b of Method of the Invention)

A cysteine molecule 90 was labelled using linker molecule 31 in the following protocol.

Linker molecule 31 (1.2 mg) was dissolved in Ammonia 7M in Methanol. N-acetyl cysteine (Compound 90) (3 mg, 2.25 eq.) was added and mixture was stirred at room temperature for 2 hours. After reaction, compound 32 was formed, which was concentrated under pressure.

2) Schiff Base Reversal (Step c of Method of the Invention)

The Schiff base of compound 32 was hydrolysed in the following protocol. Compound 32 was dissolved in release buffer (release buffer: 231 mg $NH_2OH$ in 200 μl Ammonium buffer pH6) and heated at 50° C. for 1 hour. The products (compounds 33, 22) were purified by injection HPLC (analytical 0-60% ACN over 40 min and 100% ACN for 10 min).

The method of labelling an amino acid according to this Example of the invention shows that the method of the invention may be applied to label and release, and/or relabel, amino acids containing a thiol moiety other than cysteine.

Moreover, this Example illustrates that peptides comprising amino acids containing a thiol moiety (e.g. cysteine) may be labelled and released, and relabeled, according to embodiments of the invention.

Advantageously, the method according to the invention is bio-orthogonal, that is, it may be performed in a biological system without interfering with the native biochemical processes. More advantageously, once reversed, the modification made to a biomolecule, e.g. a polynucleotide biomolecule, for example, DNA, is relatively small and hydrophilic meaning it will not affect the way that the biomolecule interacts in solution or with enzymes.

The linker molecule comprises a hydrolysable moiety, e.g. a Schiff base moiety, which is hydrolysable such that a label may be reversibly conjugated to the biomolecule. Advantageously, the conditions required to hydrolyse the Schiff base moiety are mild, which does not damage the structure of the biomolecule. Moreover, Schiff base chemistry is not commonly found in biomolecules, unlike prior art approaches such as the use of disulphide linkages. More advantageously, Schiff bases such as oximes and hydrazones are stable at physiological pH.

The covalent bonds formed using the linker molecule are reversible and rewritable. Advantageously, the label molecule may be used for repeated modifications of biomolecules, for example, labelling, capture, release, refunctionalisation for, e.g. fluorescent labelling, and/or imaging.

The analogue of S-adenosyl-1-methionine cofactor may be designed to comprise a linker molecule of any suitable structure.

Advantageously, the second functional group of the linker molecule is usable to further functionalise the biomolecule, e.g. polynucleotide, for example using click chemistry. This may be used for DNA capture, DNA complexation, drug attachment, and/or fluorescent labelling.

It will be appreciated by those skilled in the art that several variations to the aforementioned embodiments are envisaged without departing from the scope of the invention. For example, the biomolecule need not be a polynucleic acid. In embodiments, the first functional group of the linker molecule may be selected to be able to react with a moiety on a different biomolecule to form a covalent bond. For example, the biomolecule may comprise an azide moiety, and the first functional group may comprise an alkyne moiety, or vice versa, that is capable of forming a covalent bond via click chemistry.

It will also be appreciated by those skilled in the art that any number of combinations of the aforementioned features and/or those shown in the appended drawings provide clear advantages over the prior art and are therefore within the scope of the invention described herein.

The invention claimed is:

1. A method of reversibly labeling a biomolecule, the method comprising the steps of:

a. providing a linker molecule, the linker molecule comprising a first functional group comprising a reactive center, a second functional group comprising a reactive center, and a cleavable moiety;

b. forming a covalent bond between the biomolecule and the reactive center of the first functional group;

C. forming a covalent bond between a first label and the reactive center of the second functional group;

d. cleaving the cleavable moiety of the linker molecule to remove the first label and to form a third functional group comprising a reactive center; and e. forming a covalent bond between a further molecule and the reactive center of the third functional group to reform the cleavable moiety;

wherein the further molecule comprises a fourth functional group;

wherein the biomolecule is a polynucleotide or a peptide; and wherein the linker molecule has the following general formula:

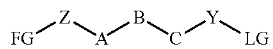

wherein FG represents the second functional group which is selected from one of F, Cl, Br, I, an alkene, an alkyne, an azide, an activated ester, an activated carbonate, a carbamate, an epoxide, an isothiocyanate, and an isocyanate moiety;

Z represents a non-reactive group selected from one of an aliphatic linkage or an aromatic linkage;

A-B—C together represent the cleavable moiety;

Y represents a non-reactive group of an aliphatic linkage or an aromatic linkage;

LG represents a first functional group comprising a reactive center, wherein LG is i) an S-Adenosyl-L-homocysteine moiety such that the linker molecule has the following general formula:

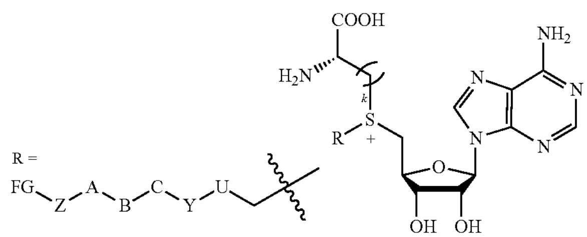

wherein U represents an unsaturated bond selected from one of an alkene, an alkyne, an aryl group, a carbon atom comprising a carbonyl group, a sulphur atom comprising one or two S═O bonds; or ii) a halogen, and wherein the cleavable moiety A-B—C represents one of the following moieties:

(i)

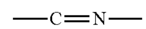

(ii)

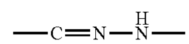

(iii)

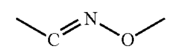

(iv)

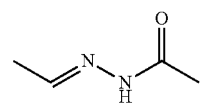

(v)

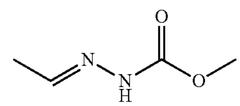

-continued (vi)

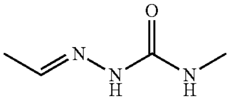

(vii)

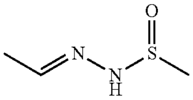

(viii)

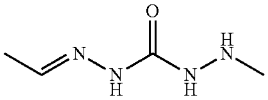

(ix)

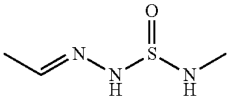

(x)

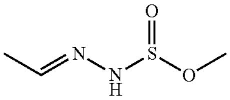

(xi)

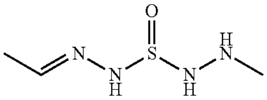

(xii)

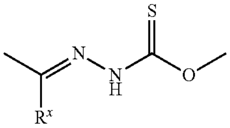

(xiii)

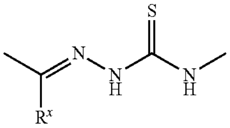

(xiv)

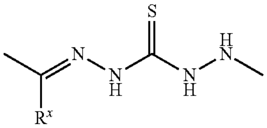

(xv)

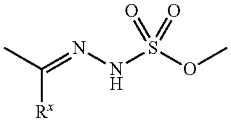

(xvi)

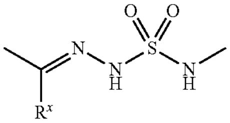

(xvii)

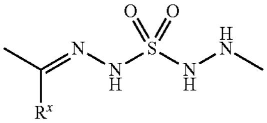

wherein $R^x$ represents a hydrogen atom, a deuterium atom, an aliphatic linkage, or an aromatic linkage.

2. The method according to claim 1, wherein the method further comprises step f. forming a covalent bond between a second label and a reactive center of the fourth functional group.

3. The method according to claim 2, wherein the method further comprises step g. cleaving the cleavable moiety to remove the second label and to reform the third functional group.

4. The method according to claim 3, wherein the method further comprises step h. forming a covalent bond between a further molecule and the third functional group to reform the cleavable moiety, wherein the further molecule of step e. is optionally the same species as the further molecule of step h.

5. The method according to claim 1, wherein the further molecule comprises a second label.

6. The method according to claim 1, wherein Z represents a polyether chain.

7. The method according to claim 1, wherein the biomolecule is a polynucleotide.

8. The method according to claim 1, wherein step b. forming a covalent bond between the biomolecule and the reactive center of the first functional group further comprises the step of providing a catalyst.

9. The method according to claim 8, wherein the catalyst is an enzyme.

10. The method according to claim 1, wherein the linker molecule is an analogue of an S-adenosyl-1-methionine cofactor and has the following general formula:

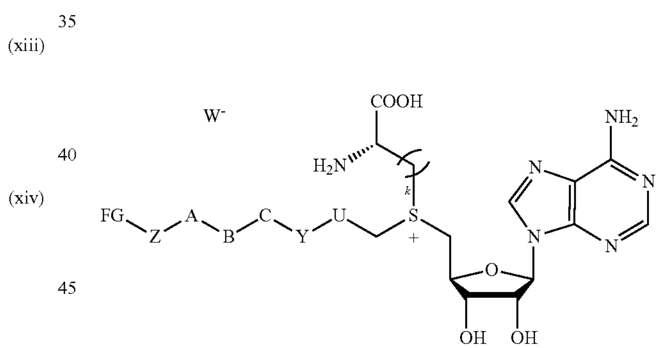

wherein FG represents the second functional group;

Z represents a non-reactive group of an aliphatic linkage or an aromatic linkage;

A-B—C represent the cleavable moiety;

Y represents a non-reactive group of an aliphatic linkage or an aromatic linkage;

U represents an unsaturated bond comprising at least one of an alkene, an alkyne, an aryl group, a carbon atom comprising a carbonyl group, and a sulfur atom comprising one or two S═O bonds;

k represents an integer of 1 or 2; and $W^-$ is a counter ion.

11. The method according to claim 10, wherein the linker molecule comprises an unsaturated moiety U.

12. The method according to claim 10, wherein the linker molecule has one of the following general formulas:

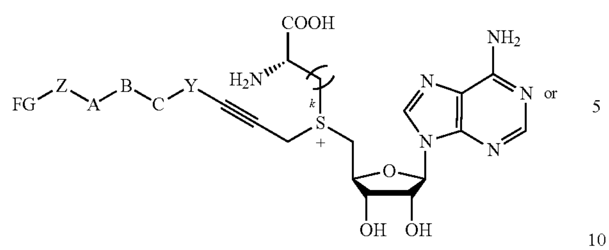

or

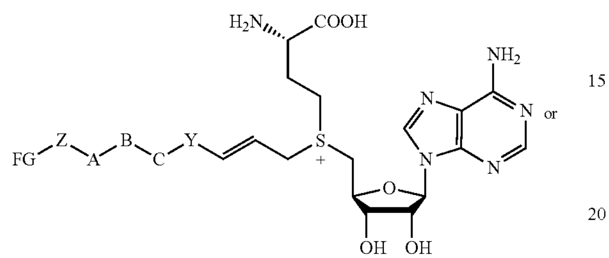

or

-continued

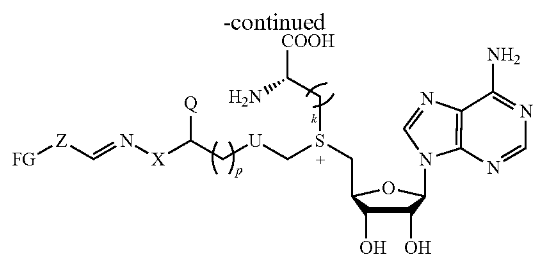

wherein the cleavable moiety is a Schiff base moiety comprising C═N—X—C-Q;

p represents a number between 1 to 15;

Q represents an oxygen atom, two hydrogen atoms, or one or more deuterium atoms independently bonded to the carbon center;

X represents an oxygen atom or a nitrogen atom;

Z represents a non-reactive group of an aliphatic linkage or an aromatic linkage;

k represents an integer of 1 or 2; and

FG represents the second functional group or

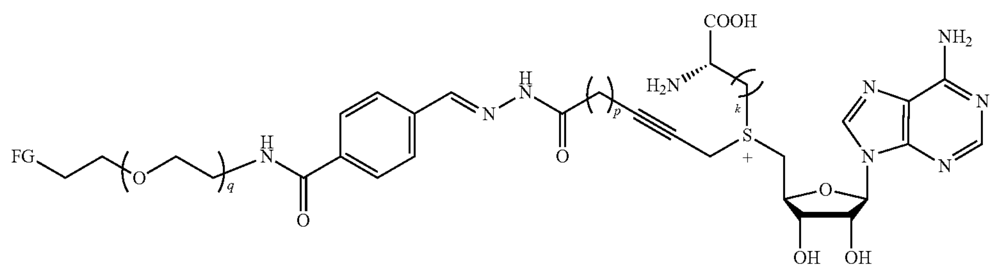

wherein the cleavable moiety is a Schiff base moiety comprising —C═N—N—C═O;

p represents a number between 1 to 15;

q represents a number between 1 to 15;

k represents an integer of 1 or 2; and

FG represents the second functional group;

or

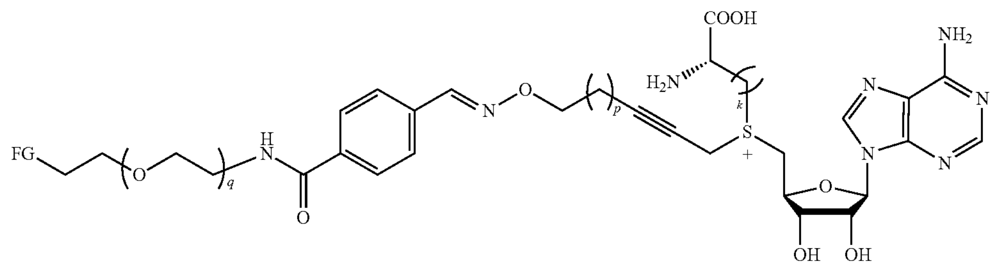

wherein the cleavable moiety is a Schiff base moiety comprising —C═N—O—;

p represents a number between 1 to 15;

wherein q represents a number between 1 to 15;

k represents an integer of 1 or 2; and

FG represents the second functional group.

13. The method according to claim 1, wherein the first functional group LG represents a halogen for reaction with an amino acid, a peptide, or a protein and/or the second functional group FG is an azide moiety.

14. The method according to claim 1, wherein forming a covalent bond between a first label and the reactive center of the second functional group comprises a reaction of an azide moiety with an alkyne moiety to form a carbon-nitrogen covalent bond.

15. The method according to claim 1, wherein cleaving the cleavable moiety of the linker molecule to remove a label and to form a third functional group comprises treatment with hydroxylamine.

16. The method according to claim 2, wherein at least one of the first label and the second label comprises at least one of a fluorescent molecule, a radioactive species, and a biological molecule.

17. The method according to claim 1, wherein forming a covalent bond between a further molecule and the third functional group in step e., to reform the cleavable moiety further comprises a reaction of an $NH_2$ moiety with an aldehyde moiety on the further molecule to form a carbon-nitrogen double bond.

18. A method of reversibly labeling a polynucleotide molecule, the method comprising the steps of:

a. providing a linker molecule (Compound A) having the following general formula:

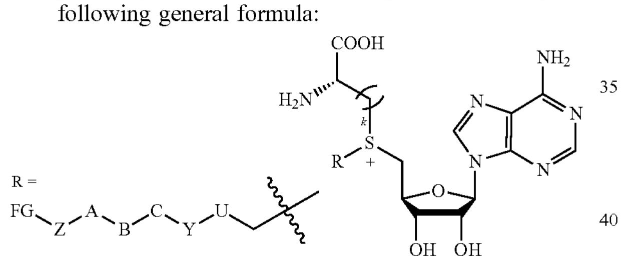

wherein R represents a transferable group;

FG represents a second functional group;

Z represents a non-reactive group of an aliphatic linkage or an aromatic linkage;

A-B—C represent a cleavable moiety;

Y represents a non-reactive group of an aliphatic linkage or an aromatic linkage;

U represents an unsaturated bond selected from the group consisting of an alkene, an alkyne, an aryl group, a carbon atom comprising a carbonyl group, and a sulfur atom comprising one or two S═O bonds;

k represents an integer of 1 or 2; and b. forming a covalent bond between the polynucleotide molecule and the R group of Compound A using a DNA methyltransferase enzyme which is capable of using Compound A as a cofactor and under conditions that allow for the transfer of the R group of Compound A onto the polynucleotide molecule;

c. forming a covalent bond between a first label and the second functional group FG of Compound A;

d. hydrolyzing the cleavable moiety or hydrolyzable moiety of the linker molecule to remove the first label and to form an O-substituted hydroxylamine or an N-substituted hydrazone;

e. forming a covalent bond between an aldehyde moiety of a further molecule and the O-substituted hydroxylamine or the N-substituted hydrazone to reform a Schiff base moiety, wherein the further molecule comprises a fourth functional group.

* * * * *